(12) United States Patent
Eckert et al.

(10) Patent No.: US 7,811,578 B2
(45) Date of Patent: *Oct. 12, 2010

(54) SOLUBLE CHIMERIC PEPTIDE INHIBITORS OF HIV ENTRY COMPRISING AN IZ TRIMERIC COILED-COIL PEPTIDE AND HIV GP41 N-HELIX COILED-COIL PEPTIDE

(75) Inventors: Debra M. Eckert, Salt Lake City, UT (US); Tara R. Suntoke, Pasadena, CA (US); Peter S. Kim, Bryn Mawr, PA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 11/786,764

(22) Filed: Apr. 12, 2007

(65) Prior Publication Data

US 2008/0269462 A1 Oct. 30, 2008

Related U.S. Application Data

(63) Continuation of application No. 10/395,817, filed on Mar. 21, 2003, now Pat. No. 7,226,598, which is a continuation of application No. PCT/US01/29637, filed on Sep. 21, 2001, which is a continuation of application No. 09/668,072, filed on Sep. 22, 2000, now Pat. No. 6,747,126, which is a continuation-in-part of application No. 09/364,497, filed on Jul. 30, 1999, now Pat. No. 6,818,740, said application No. 10/395,817 is a continuation of application No. 09/746,742, filed on Dec. 21, 2000, now Pat. No. 6,841,657, which is a continuation of application No. PCT/US99/17351, filed on Jul. 30, 1999.

(60) Provisional application No. 60/132,295, filed on May 3, 1999, provisional application No. 60/101,058, filed on Sep. 18, 1998, provisional application No. 60/100,265, filed on Sep. 14, 1998, provisional application No. 60/094,676, filed on Jul. 30, 1998.

(51) Int. Cl.
*A61K 39/00* (2006.01)
*A61K 39/21* (2006.01)

(52) U.S. Cl. ............... 424/192.1; 424/188.1; 424/208.1

(58) Field of Classification Search ........................ None
See application file for complete search history.

(56) References Cited

U.S. PATENT DOCUMENTS

| | | | |
|---|---|---|---|
| 5,444,044 A | 8/1995 | Jiang et al. | |
| 5,464,933 A | 11/1995 | Bolognesi et al. | |
| 5,656,480 A | 8/1997 | Wild et al. | |
| 5,780,221 A | 7/1998 | Schumacher et al. | |
| 5,840,843 A | 11/1998 | Jiang et al. | |
| 6,150,088 A | 11/2000 | Chan et al. | |
| 6,506,554 B1 | 1/2003 | Chan et al. | |
| 6,747,126 B1 * | 6/2004 | Eckert et al. | 530/324 |
| 6,818,740 B1 | 11/2004 | Eckert et al. | |
| 6,841,657 B2 | 1/2005 | Eckert et al. | |
| 7,053,179 B2 | 5/2006 | Root et al. | |
| 7,226,598 B2 * | 6/2007 | Eckert et al. | 424/188.1 |
| 7,402,396 B2 | 7/2008 | Chan et al. | |
| 7,504,224 B2 | 3/2009 | Root et al. | |
| 2001/0047080 A1 | 11/2001 | Root et al. | |
| 2002/0077284 A1 | 6/2002 | Eckert et al. | |
| 2003/0082525 A1 | 5/2003 | Root et al. | |
| 2003/0099935 A1 | 5/2003 | Chan et al. | |
| 2004/0044183 A1 | 3/2004 | Eckert et al. | |
| 2004/0213801 A1 | 10/2004 | Wild et al. | |
| 2005/0053917 A1 | 3/2005 | Chan et al. | |
| 2005/0221294 A1 | 10/2005 | Eckert et al. | |
| 2006/0014139 A1 | 1/2006 | Root et al. | |

FOREIGN PATENT DOCUMENTS

| | | |
|---|---|---|
| WO | WO 94/02505 | 2/1994 |
| WO | WO 96/40191 | 12/1996 |
| WO | WO 98/32848 | 7/1998 |
| WO | WO 00/06599 | 2/2000 |
| WO | WO 00/40616 | 7/2000 |
| WO | WO 01/03723 A1 | 1/2001 |
| WO | WO 01/44286 A2 | 6/2001 |
| WO | WO 02/24735 A2 | 3/2002 |
| WO | WO 02/24735 A3 | 3/2002 |

OTHER PUBLICATIONS

Manchester, M., et al., 1994, Identification of temperature-sensitive mutants of the human immunodeficiency virus type 1 protease through saturation mutagenesis, J. Biol. Chem. 269(10):7689-7695.*

(Continued)

*Primary Examiner*—Jeffrey S. Parkin
(74) *Attorney, Agent, or Firm*—Hamilton, Brook, Smith & Reynolds, P.C.

(57) ABSTRACT

Described herein are chimeric peptides comprising a soluble trimeric coiled-coil and all or a portion of the N-peptide region of HIV gp41. These molecules are stable, trimeric coiled-coils that inhibit HIV entry into cells, such as human cells. Such peptides can be further assessed to demonstrate their ability to serve as potent anti-HIV therapeutic molecules and thus, as therapeutic molecules or drugs.

9 Claims, 11 Drawing Sheets
(8 of 11 Drawing Sheet(s) Filed in Color)

OTHER PUBLICATIONS

Cao, J., et al., 1993, Effects of amino acid changes in the extracellular domain of the human immunodeficiency virus type 1 gp41 envelope glycoprotein, J. Virol. 67(5):2747-2755.*

Moschella, F., et al., Administration of different antigenic forms of altered peptide ligands derived from HIV RTase influences their effects on T helper cell activation, Human Immunol. 64:1-8.*

Eckert, D.M., and Kim, P.S., "Design of Potent Inhibitors of HIV-1 Entry from the gp41 N-peptide Region," *PNAS*, 98(20):11187-11192 (Sep. 25, 2001).

Chen, et al., "Mutations in the leucine zipper-like heptad repeat sequence of Human Immunodeficiency Virus Type 1 gp41 Dominantly Interfere with Wild-Type Virus Infectivity," *J. of Virology*, 72(6): 4765-4774 (1998).

Kliger et al., "Inhibition of HIV-1 Entry Before gp41 Folds into its Fusion-Active Conformation," *J. of Mol. Biol.*, 295: 163-168 (2000).

Bahbouhi, B., et al., "Effects of L-and D-REKR Amino Acid-Containing Peptides on HIV and SIV Envelope Glycoprotein Precursor Maturation and HIV and SIV Replication," *Biochem. J.* 366 (Pt. 3):863-872 (2002).

Baum, Rudy, "Virus-cell Fusion Targeted for Drug Development," C&EN (May 13, 1996).

Benkirane, M., et al., "Antigenicity and Immunogenicity of Modified Synthetic Peptides Containing D-Amino Acid Residues. Antibodies to a D-Enantiomer Do Recognize the Parent L-Hexapeptide and Reciprocally," J. Biol. Chem. 268(35): 26279-26285 (1993).

Bernstein, H.B., et al., "Oligomerization of the Hydrophobic Heptad Repeat of gp41," *Journal of Virology*, 69(5):2745-2750 (1995).

Blacklow, Stephen C., et al., "A Trimeric Subdomain of the Simian Immunodeficiency Virus Envelope Glycoprotein," *Biochemistry*, 34(46): 14955-14962 (1995).

Blake, James and Li, Choh Hao, "Adrenocorticotropin. 47. Synthesis and Biological Activity of Adrenocorticotropic Peptides Modified at the Tryptophan Position," *J. Medicinal Chem.* 18(4):423-426 (1975).

Borchardt, Allen et al., "Small Molecule-dependent genetic selection in stochastic nanodroplets as a means of detecting protein-ligand interactions on a large scale," *Chem. & Biol.* 4(12):961-968 (1997).

Bowie, J.U., et al., "Deciphering the Message in Protein Sequences: Tolerance to Amino Acid Substitutions," *Science*, 247: 1306-1310 (1990).

Bullough, Per A. et al., "Structure of influenza haemagglutinin at the pH of membrane fusion," *Nature 371*:37-43 (1994).

Buttó, C., et al., "Dual infection with different strains of the same HIV-1 subtype", AIDS, vol. II, No. 5:694-696 (1997).

Caffrey, Michael et al., "Three-dimensional solution structure of the 44kDa ectodomain of SIV gp41," *EMBO J.* 17(16):4572-4584 (1998).

Cao, Jie et al., "Effects of Amino Acid Changes in the Extracellular Domain of the Human Immunodeficiency Virus Type 1 gp41 Envelope Glycoprotein," *J. Virology* 67(5):2747-2755 (1993).

Chabala, John C., "Solid-phase combinatorial chemistry and novel tagging methods for identifying leads," *Curr. Opin. Biotech.* 6:632-639 (1995).

Chakrabartty, Avijit et al., "Aromatic Side-Chain Contribution to Far-Ultraviolet Circular Dichroism of Helical Peptides and Its Effect on Measurement of Helix Propensities," *Biochemistry 32*:5560-5565 (1993).

Chambers, Philip, et al., "Heptad Repeat Sequences are Located Adjacent to Hydrophobic Regions in Several Types of Virus Fusion Glycoproteins," *Journal of General Virology*, 71:3075-3080 (1990).

Chan, D.C. and Kim, P.S., "HIV Entry and Its Inhibition," *Cell* 93:681-684 (1998).

Chan, David C., et al., "Core Structure of gp41 from the HIV Envelope Glycoprotein," *Cell 89*:263-273 (1997).

Chan, D.C., et al., "Evidence that a prominent cavity in the coiled coil of HIV type 1 gp41 is an attractive drug target," *Proc. Natl. Sci. USA*, 95:15613-15617 (1998).

Chang, Ding-Kwo, et al., "Proline Affects Oligomerization of a Coiled Coil by Inducing a Kink in a Long Helix," *Journal of Structural Biology*, 128:270-279 (1999).

Chen, Benjamin K. et al., "Distinct Modes of Human Immunodeficiency Virus Type 1 Proviral Latency Revealed by Superinfection of Nonproductively Infected Cell Lines with Recombinant Luciferase-Encoding Viruses," *J. Virology* 68(2):654-660 (1994).

Chen, Charlie L. et al., "One Bead-One Compound Combinatorial Peptide Library: Different Types of Screening," *Methods in Enzymology 267*:211-219 (1996).

Chen, Chin-Ho et al., "A Molecular Clasp in the Human Immunodeficiency Virus (HIV) Type 1 TM Protein Determines the Anti-HIV Activity of gp41 Derivatives:Implication for Viral Fusion," *J. Virology 69*(6):3771-3777 (1995).

Chen, Yee-Hsiung et al., "Determination of the Helix and β Form of Proteins in Aqueous Solution by Circular Dichroism," *Biochemistry 13*(16):3350-3359 (1974).

Cole, James L. and Garsky, Victor M., "Thermodynamics of Peptide Inhibitor Binding to HIV-1 gp41," *Biochemistry 40*:5633-5641 (2001).

Corigliano-Murphy, M.A., et al., "Synthesis and Properties of an All-D Model Ribonuclease S-Peptide," Int. J. Pep. Prot. Res. 25:225-231 (1985).

Delwart, Eric L., et al., "Retroviral Envelope Glycoproteins Contain a 'Leucine Zipper'-like Repeat," *AIDS Research and Human Retroviruses*, 6(6):703-706 (1990).

Doering Don S. and Matsudaira, Paul, "Cysteine Scanning Mutagenesis at 40 of 76 Positions in Villin Headpiece Maps the F-Actin Binding Site and Structural Features of the Domain," *Biochemistry 35*:12677-12685 (1996).

Dutch, Rebecca Ellis et al., "Paramyxovirus Fusion Protein: Characterization of the Core Trimer, a Rod-Shaped Complex with Helices in Anti-Parallel Orientation," *Virology 254*:147-159 (1999).

Eckert, D.M. and Kim, P.S., "Mechanisms of Viral Membrane Fusion and Its Inhibition," Annu. Rev. Biochem., 70:777-810 (2001).

Eckert, Debra M. et al., "Crystal Structure of GCN4-p1$_Q$l, a Trimeric Coiled Coil with Buried Polar Residues," *J. Mol. Biol. 284*:859-865 (1998).

Eckert, Debra M., et al., "Inhibiting HIV-1 Entry: Discovery of D-Peptide Inhibitors that Target the gp41 Coiled-Coil Pocket,"*Cell*, 99:103-115 (1999).

Eckhart, Leopold et al., "Immunogenic Presentation of a Conserved gp41 Epitope of Human Immunodeficiency Virus Type I on Recombinant Surface Antigen of Hepatitis B Virus," J. Gen. *Virol. 77*:2001-2008 (1996).

Edelhoch, Harold, "Spectroscopic Determination of Tryptophan and Tyrosine in Proteins," *Biochemistry 6*:(7):1948-1954 (1967).

Fahey, J.L. and Schooley, R., "Status of immune-based therapies in HIV infection and AIDS", Clin. Exp. Immunol., 88:1-5 (1992).

Fass, Deborah and Kim, Peter S., "Dissection of a Retrovirus Envelope Protein Reveals Structural Similarity to Influenza Hemagglutinin," *Current Biology*, 5(12):1-7 (1995).

Fass, Deborah et al., "Retrovirus envelop domain at 1.7 □ resolution," *Nature Structural Biology 3*(5):465-469 (1996).

Ferrer, Marc et al., "Selection of gp41-mediated HIV-1 cell entry inhibitors from biased combinatorial libraries of non-natural binding elements," Nature Structural Biology 6(10):953-960 (1999).

Furuta et al., "Capture of an early fusion-active conformation of HIV-1 gp41," *Nature Structural Biology* 5(4):276-279 (1998).

Gallaher, William R., et al., "A General Model for the Transmembrane Proteins of HIV and Other Retroviruses," *Aids Research and Human Retroviruses*, 5(4):431-440 (1989).

Harbury, Pehr B. et al., "Crystal structure of an isoleucine-zipper trimer," *Nature 371*:80-83 (1994).

Harbury, Pehr B. et al., "Repacking protein cores with backbone freedom:Structure prediction for coiled coils," *Proc. Natl. Acad. Sci, USA 92*:8408-8412 (1995).

Hirsch, Vanessa M. and Johnson, Philip R., "Pathogenic diversity of simian immunodeficiency viruses," *Virus Research 32*:183-206 (1994).

Hooft, Rob W.W. and Vriend, Gert, "Errors in protein structures," *Nature 381*:272 (1996).

Jiang, S., et al., "A screening assay for antiviral compounds targeted to the HIV-1 gp41 core structure using a conformation-specific monoclonal antibody," *J. Virol. Methods 80*(1):85-96 (1999).

Jiang, Shibo et al., "A conformation-Specific Monoclonal Antibody Reacting with Fusion-Active gp41 from the Human Immunodeficiency Virus Type 1 Envelope Glycoprotein," *J. Virology* 72(12):10213-10217 (1998).

Jiang, Shibo et al., "Development of HIV Entry Inhibitors Targeted to the Coiled-Coil Regions of gp41," Biochemical and Biophysical Research Communications 269(3):641-646 (2000).

Jiang, Shibo et al., "HIV-1 inhibition by a peptide," *Nature 365*:113 (1993).

Jones, T.A. et al., "Improved Methods for Building Protein Models in Electron Density Maps and the Location of Errors in these Models," *Acta Cryst.* A47:110-119 (1991).

Joyce, J.G., et al., "Enhancement of α-Helicity in the HIV-1 Inhibitory Peptide DP178 Leads to an Increased Affinity for Human Monoclonal Antibody 2F5 but Does Not Elicit Neutralizing Responses in Vitro," *Journal of Biological Chemistry*, 277(48):45811-45820 (2002).

Judice, J.K., et al., Inhibition of HIV type 1 infectivity by constrained α-helical peptides: Implications for the viral fusion mechanism, *Proc. Natl. Acad. Sci. USA*, 94:13426-13430 (1997).

Kilby, J.M., et al., "Potent suppression of HIV-1 replication in humans by T-20, a peptide inhibitor of gp41-mediated virus entry," *Nature Medicine* 4(11):1302-1307 (1998).

Kliger, Yossef et al., "Mode of Action of an Antiviral Peptide from HIV-1, "*J. Biol. Chem.* 276(2):1391-1397 (2001).

Kozarsky, Karen et al., "Glycosylation and Processing of the Human Immunodeficiency Virus Type 1 Envelope Protein," J. Acquired Immune Deficiency Syndromes 2:163-169 (1989).

Kramer, A., et al., "Stepwise Transformation of a Cholera Toxin and a p24 (HIV-1) Epitope Into D-Peptide Analogs," Prot. Engin. 11(10):941-948 (1998).

Kubinyi, Hugo, "Combinatorial and computational approaches in structure-based drug design," *Curr. Op. In Drug Disc. & Dev.* 1(1):16-22 (1998).

Kuntz, Irwin D., "Structure-Based Strategies for Drug Design and Discovery," *Science*, 257:1078-1082 (1992).

LaCasse, Rachel A. et al., "Fusion-Competent Vaccines: Broad Neutralization of Primary Isolates of HIV," *Science 283*:357-362 (1999).

Lam, Kit S. et al., "A new type of synthetic peptide library for identifying ligand-binding activity," *Nature 354*:82-84 (1991).

Lambert, D.M. et al., "Peptides from conserved regions of paramyxovirus fusion (F) proteins are potent inhibitors of viral fusion," *Proc. Natl. Acad. Sci. USA* 93:2186-2191 (1996).

Letvin, Norman L., "Progress in the Development of an HIV-1 Vaccine," *Science 280*:1875-1880 (1998).

Levy, R.B., et al., "T Lymphocytes Can Recognize Determinants Unique to Neuropeptides of Guinea Pig Myelin Basic Protein Containing a Single D-Isomer Amino Acid Substitution," J. Neuro. Res. 25(1):29-38 (1990).

Li, Zhe, et al., "Anti-malarial Drug Development Using Models of Enzyme Structure," *Chemistry & Biology*, 1:31-37 (1994).

Lu, Min and Kim, Peter S., "A Trimeric Structural Subdomain of the HIV-1 Transmembrane Glycoprotein," *J. Biomol. Structure & Dynamics 15*(3):465-471 (1997).

Lu, Min, et al., "A Trimeric Structural Domain of the HIV-1 transmembrane glycoprotein," *Nature Structural Biology*, 2(12):1-8 (1995).

Malashkevich, Vladimir N. et al., "Core structure of the envelope glycoprotein GP2 from Ebola virus at 1.9-Å resolution," *Proc. Natl. Acad. Sci. USA 96*:2662-2667 (1999).

Malashkevich, Vladimir N. et al., "Crystal structure of the simian immunodeficiency virus (SIV) gp41 core: Conserved helical interactions underlie the broad inhibitory activity of gp41 peptides," *Proc. Natl. Acad. Sci. USA 95*:9134-9139 (1998).

Manchester, M., et al., "Identification of temperature-sensitive mutants of the human immunodeficiency virus type 1 protease through saturation mutagenesis," *J. Biol. Chem.*, 269(1):7689-7695 (1994).

Meng, Elaine C., et al., "Automated Docking with Grid-Based Energy Evaluation," *Journal of Computational Chemistry*, 13(4):505-524 (1992).

Miller, M.D., "A Human Monoclonal Antibody Blocks HIV Entry by a T20-Like Mechanism," *Merck Research Laboratories*, Abstract presented at the 13th International HIV Drug Resistance Workshop, Jun. 8-12, 2004, Tenerife, Canary Islands, Spain.

Miller, M.D., "A Human Monoclonal Antibody Neutralizes Diverse HIV-1 Isolates by Binding a Critical gp41 Epitope," *P.N.A.S. USA 102*:14759-14764 (2005).

Moschella, F., et al., "Administration of different antigenic forms of altered peptide ligands derived from HIV-1 RTase influences their effects on T helper cell activation," *Hum. Immunol.*, 64:1-8 (2003).

Muster, Thomas et al., "A Conserved Neutralizing Epitope on gp41 of Human Immunodeficiency Virus Type 1," J. Virology 67(11):6642-6647 (1993).

Muster, Thomas et al., "Cross-Neutralizing Activity against Divergent Human Immunodeficiency Virus Type 1 Isolates Induced by the gp41 Sequence ELDKWAS," J. Virology 68(6):4031-4034 (1994).

Nautiyal, Shivani and Alber, Tom, "Crystal structure of a designed, thermostable, heterotrimeric coiled coil," Protein Science 8:84-90 (1999).

Nolte, Alexis et al., "Mirror-design of L-oligonucleotide ligands binding to L-arginine," Nature Biotechnology 4:1116-1119 (1996).

O'Neil, Karyn T. and DeGrado, William F., "A Thermodynamic Scale for the Helix-Forming Tendencies of the Commonly Occurring Amino Acids," Science 250:646-351 (1990).

Poumbourios, P., et al., "Human Immunodeficiency Virus Type 1 Envelope Glycoprotein Oligomerization Requires the gp41 Amphipathic α-Helical/Leucine Zipper-Like Sequence," *Journal of Virology 71*(3):2041-2049 (1997).

Purtscher, Martin et al., "Restricted antigenic variability of the epitope recognized by the neutralizing gp41 antibody 2F5," AIDS 10:587-593 (1996).

Reimann, Keith A. et al., "A Chimeric Simian/Human Immunodeficiency Virus Expressing a Primary Patient Human Immunodeficiency Virus Type 1 Isolate env Causes an AIDS-Like Disease after In Vivo Passage in Rhesus Mondkeys," J. Virology 70(10):6922-6928 (1996).

Richman, D.D., "Nailing down another HIV target, "*Nature Medicine*, 4 (11):1232-1233 (1998).

Richman, Douglas, D. et al., "Rapid Evolution of the neutralizing antibody response to HIV type 1 infection," Proc.Natl.Acd.Sci., 100(7):4144-4149 (2003).

Rimsky, Laurence T. et al., "Determinants of Human Immunodeficiency Virus Type I Resistance to gp41-Derived Inhibitory Peptides," J. Virology 72(2):986-993 (1998).

Ring, Christine S., et al., "Structure-based Inhibitor Design by Using Protein Models for the Development of Antiparasitic Agents," *Proc. Natl. Acad. Sci. USA*, 90:3583-3587 (1993).

Root, Michael J. et al., "Protein Design of an HIV-1 Entry Inhibitor," Science 291:884-888 (2001).

Rudinger, J.A., "Characteristics of the Amino Acids as Components of a Peptide Hormone Sequence," *In Peptide Hormones*, Ed. JA Parsons, pp. 1-6 (Jun. 1976).

Schumacher, Ton N.M. et al., "Identification of D-Peptide Ligands Through Mirror-Image Phage Display," Science 271:1854-1857 (1996).

Shuker, Suzanne B. et al., "Discovering High-Affinity Ligands for Proteins: SAR by NMR," Science 274:1531-1534 (1996).

Singh, Mona et al., "LearnCoil-VMF: Computational Evidence for Coiled-coil-like Motifs in Many Viral Membrane-fusion Proteins," J. Mol. Biol. 290:1031-1041 (1999).

Tan, Kemin et al., "Atomic structure of a thermostable subdomain of HIV-1 gp41," Proc. Natl. Acad. Sci. USA 94:12303-12308 (1997).

Tarrago-Litvak, Laura et al., "The reverse transcriptase of HIV-1: from enzymology to therapeutic intervention," FASEB J. 8:497-503 (1994).

Tucker, Thomas J. et al., "Development of Nonnucleoside HIV Reverse Transcriptase Inhibitors," Methods in Enzymology 275:440-472 (1996).

Tyagi, Sanjay et al., "Multicolor molecular beacons for allele discrimination," Nature Biotechnology 16:49-53 (1998).

Weissenhorn, W. et al., "Atomic structure of the ectodomain from HIV-1 gp41," Nature 387:426-430 (1997).

Weissenhorn, W., et al., Assembly of a rod-shaped chimera of a trimeric GCN4 zipper and the HIV-1 gp41 ectodomain expressed in *Escherichia coli, Proc. Natl. Acad. Sci. USA*, 94:6065-6069 (1997).

Weissenhorn, Winfried et al., "Crystal Structure of the Ebola Virus Membrane Fusion Subunit, GP2, from the Envelope Glycoprotein Ectodomain," Molecular Cell 2:605-616 (1998).

Weng, Y., et al., "Mutational Analysis of Residues in the Coiled-Coil Domain of Human Immunodeficiency Virus Type 1 Transmembrane Protein gp41," J. Virol. 72(12):9676-9682 (1998).

Wild, Carl et al., "A synthetic peptide inhibitor of human immunodeficiency virus replication: Correlation between solution structure and viral inhibition," Proc. Natl. Acad. Sci. USA 89:10537-10541 (1992).

Wild, Carl T. et al., "Peptides corresponding to a predictive α-helical domain of human immunodeficiency virus type 1 gp41 are potent inhibitors of virus infection," Proc. Natl. Acad. Sci. USA 91:9770-9774 (1994).

Williams, Kelly P. et al., "Bioactive and nuclease-resistant 1-DNA ligand of vasopressin," Proc Natl. Acad. Sci. USA 94:11285-11290 (1997).

Yang, Xinzhen et al., "Characterization of Stable, Soluble Trimers Containing Complete Ectodomains of Human Immunodeficiency Virus Type 1 Envelope Glycoproteins," J. Virol. 74(12):5716-5725 (2000).

Youngquist, R. Scott et al., "Generation and Screening of Combinatorial Peptide Libraries Designed for Rapid Sequencing by Mass Spectrometry," J. Am. Chem. Soc. 117:3900-3906 (1995).

Suzuki, K., et al., "An Isoleucine Zipper Peptide Forms a Native-like Triple Stranded Coiled Coil in Solution," *Protein Engineering* 11(11):1051-1055 (1998).

* cited by examiner

IQN17:
ac-RMKQIEDKIEEIESKQKKIENEIARIKKLLQLTVWGIKQLQARIL-NH2

IQN23:
ac-RMKQIEDKIEEILSKQYHIENEIARIKKLIEAQQHLLQLTVWGIKQLQARIL-NH2

Other sequences we will soon try:

IQN23, version 2:
ac-RMKQIEDKIEEIESKQKKIENEIARIKKLIEAQQHLLQLTVWGIKQLQARIL-NH2

IQN36:
ac-RMKQIEDKIEEIESKQKKIENEIARIKKLISGIVQQQNNLLRAIEAQQHLLQLTVWGIKQLQARIL-NH2 shortened versions of IQN17:
ac-EIARIKKLLQLTVWGIKQLQARIL-NH2
ac-KQKKIENEIARIKKLLQLTVWGIKQLQARIL-NH2
ac-KIKKIENEIARIKKLLQLTVWGIKQLQARIL-NH2
ac-KIEEIESKQKKIENEIARIKKLLQLTVWGIKQLQARIL-NH2
ac-KIEEIESKIKKIENEIARIKKLLQLTVWGIKQLQARIL-NH2

IQN17 with another soluble trimeric coiled coil replacing GCN4-pIQI

FIG. 2

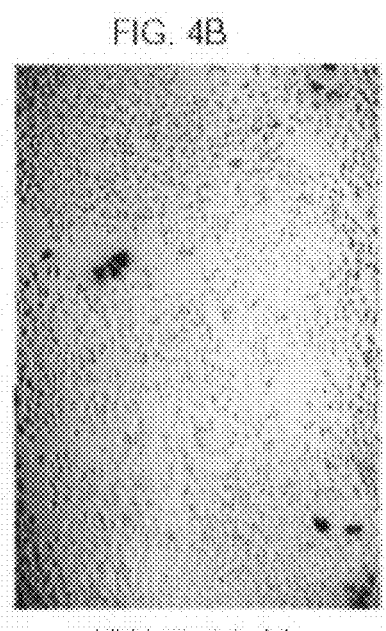
FIG. 4B
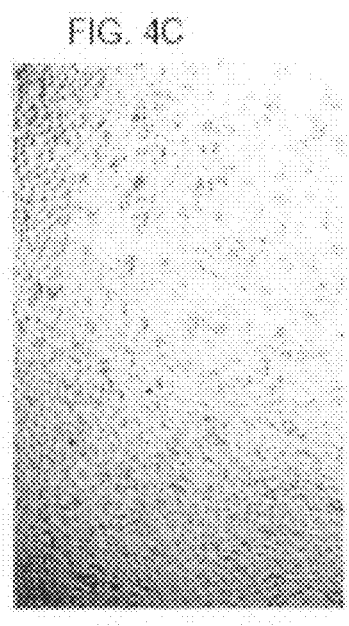
FIG. 4C
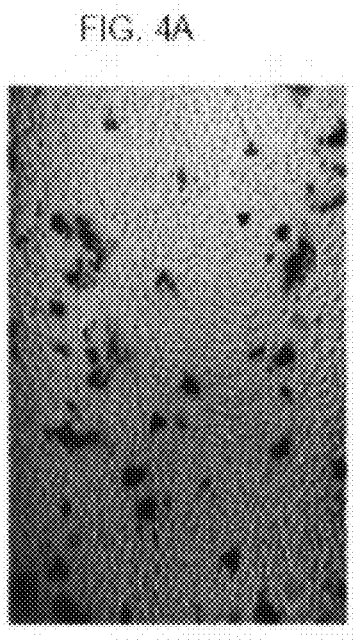
FIG. 4A
0nM
IQN17, 80nM
IQN17, 320nM
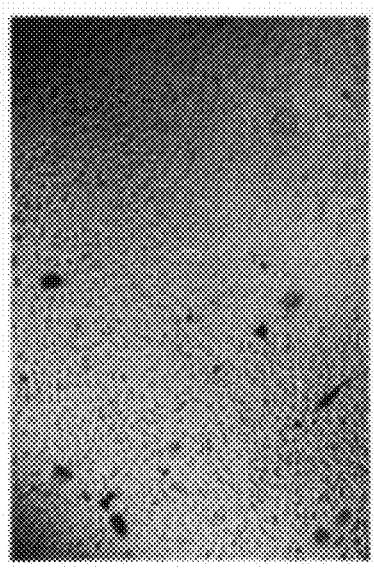
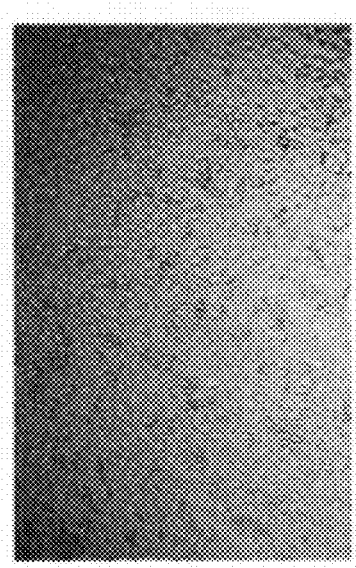
IQN23, 80nM
IQN23, 320nM
FIG. 4D
FIG. 4E GCN4-pI$_Q$I': Ac-RMKQIEDKIEEIESKQKKIENEIARIKKLIGERY-NH$_2$ IZ: Ac-YGGIKKEIEAIKKEQEAIKKKIEAIEKEIEA-NH$_2$

IQN26

Ac- R  M  K  Q  I  E  D  K  I  E  E  I  E  S  K  Q  Y  K  I  E
    Arg Met Lys Gln Ile Glu Asp Lys Ile Glu Glu Ile Glu Ser Lys Gln Tyr Lys Ile Glu

N  E  I  A  R  I  K  K  L  I  V  Q  A  R  Q  L  L  S  G  I  V
Asn Glu Ile Ala Arg Ile Lys Lys Leu Ile Val Gln Ala Arg Gln Leu Leu Ser Gly Ile Val

Q  Q  Q  N  N  L  L  R  A  I  E  A  Q  Q  H -CONH$_2$
Gln Gln Gln Asn Asn Leu Leu Arg Ala Ile Glu Ala Gln Gln His

FIG. 10

IZN26

Ac- Y  G  G  I  K  K  E  I  E  A  I  K  K  E  Q  E  A  I  K  K
    Tyr Gly Gly Ile Lys Lys Glu Ile Glu Ala Ile Lys Lys Glu Gln Glu Ala Ile Lys Lys

K  I  E  A  I  E  K  E  I  V  Q  A  R  Q  L  L  S  G  I  V
Lys Ile Glu Ala Ile Glu Lys Glu Ile Val Gln Ala Arg Gln Leu Leu Ser Gly Ile Val

Q  Q  Q  N  N  L  L  R  A  I  E  A  Q  Q  H -CONH$_2$
Gln Gln Gln Asn Asn Leu Leu Arg Ala Ile Glu Ala Gln Gln His

FIG. 11

SEQUENCE LISTING

<160> NUMBER OF SEQ ID NOS: 36

<210> SEQ ID NO 1
<211> LENGTH: 45
<212> TYPE: PRT
<213> ORGANISM: Artificial Sequence
<220> FEATURE:
<223> OTHER INFORMATION: soluble chimeric peptide IQN17
<220> FEATURE:
<221> NAME/KEY: ACETYLATION

```
<222> LOCATION: 1
<220> FEATURE:
<221> NAME/KEY: AMIDATION
<222> LOCATION: 45

<400> SEQUENCE: 1

Arg Met Lys Gln Ile Glu Asp Lys Ile Glu Glu Ile Glu Ser Lys Gln
 1               5                  10                  15

Lys Lys Ile Glu Asn Glu Ile Ala Arg Ile Lys Lys Leu Leu Gln Leu
            20                  25                  30

Thr Val Trp Gly Ile Lys Gln Leu Gln Ala Arg Ile Leu
        35                  40                  45

<210> SEQ ID NO 2
<211> LENGTH: 52
<212> TYPE: PRT
<213> ORGANISM: Artificial Sequence
<220> FEATURE:
<223> OTHER INFORMATION: soluble chimeric peptide IQN23
<220> FEATURE:
<221> NAME/KEY: ACETYLATION
<222> LOCATION: 1
<220> FEATURE:
<221> NAME/KEY: AMIDATION
<222> LOCATION: 52

<400> SEQUENCE: 2

Arg Met Lys Gln Ile Glu Asp Lys Ile Glu Glu Ile Leu Ser Lys Gln
 1               5                  10                  15

Tyr His Ile Glu Asn Glu Ile Ala Arg Ile Lys Lys Leu Ile Glu Ala
            20                  25                  30

Gln Gln His Leu Leu Gln Leu Thr Val Trp Gly Ile Lys Gln Leu Gln
        35                  40                  45

Ala Arg Ile Leu
    50

<210> SEQ ID NO 3
<211> LENGTH: 52
<212> TYPE: PRT
<213> ORGANISM: Artificial Sequence
<220> FEATURE:
<223> OTHER INFORMATION: soluble chimeric peptide IQN23, version 2
<220> FEATURE:
<221> NAME/KEY: ACETYLATION
<222> LOCATION: 1
<220> FEATURE:
<221> NAME/KEY: AMIDATION
<222> LOCATION: 52

<400> SEQUENCE: 3

Arg Met Lys Gln Ile Glu Asp Lys Ile Glu Glu Ile Glu Ser Lys Gln
 1               5                  10                  15

Lys Lys Ile Glu Asn Glu Ile Ala Arg Ile Lys Lys Leu Ile Glu Ala
            20                  25                  30

Gln Gln His Leu Leu Gln Leu Thr Val Trp Gly Ile Lys Gln Leu Gln
        35                  40                  45

Ala Arg Ile Leu
    50

<210> SEQ ID NO 4
<211> LENGTH: 66
<212> TYPE: PRT
<213> ORGANISM: Artificial Sequence
<220> FEATURE:
<223> OTHER INFORMATION: soluble chimeric peptide IQN36
```

-continued

```
<220> FEATURE:
<221> NAME/KEY: ACETYLATION
<222> LOCATION: 1
<220> FEATURE:
<221> NAME/KEY: AMIDATION
<222> LOCATION: 66

<400> SEQUENCE: 4

Arg Met Lys Gln Ile Glu Asp Lys Ile Glu Glu Ile Glu Ser Lys Gln
 1               5                  10                  15

Lys Lys Ile Glu Asn Glu Ile Ala Arg Ile Lys Lys Leu Ile Ser Gly
             20                  25                  30

Ile Val Gln Gln Gln Asn Asn Leu Leu Arg Ala Ile Glu Ala Gln Gln
         35                  40                  45

His Leu Leu Gln Leu Thr Val Trp Gly Ile Lys Gln Leu Gln Ala Arg
     50                  55                  60

Ile Leu
65

<210> SEQ ID NO 5
<211> LENGTH: 24
<212> TYPE: PRT
<213> ORGANISM: Artificial Sequence
<220> FEATURE:
<223> OTHER INFORMATION: soluble chimeric peptide IQN17, shortened
      version #1
<220> FEATURE:
<221> NAME/KEY: ACETYLATION
<222> LOCATION: 1
<220> FEATURE:
<221> NAME/KEY: AMIDATION
<222> LOCATION: 24

<400> SEQUENCE: 5

Glu Ile Ala Arg Ile Lys Lys Leu Leu Gln Leu Thr Val Trp Gly Ile
 1               5                  10                  15

Lys Gln Leu Gln Ala Arg Ile Leu
             20

<210> SEQ ID NO 6
<211> LENGTH: 31
<212> TYPE: PRT
<213> ORGANISM: Artificial Sequence
<220> FEATURE:
<223> OTHER INFORMATION: soluble chimeric peptide IQN17, shortened
      version #2
<220> FEATURE:
<221> NAME/KEY: ACETYLATION
<222> LOCATION: 1
<220> FEATURE:
<221> NAME/KEY: AMIDATION
<222> LOCATION: 31

<400> SEQUENCE: 6

Lys Gln Lys Lys Ile Glu Asn Glu Ile Ala Arg Ile Lys Lys Leu Leu
 1               5                  10                  15

Gln Leu Thr Val Trp Gly Ile Lys Gln Leu Gln Ala Arg Ile Leu
             20                  25                  30

<210> SEQ ID NO 7
<211> LENGTH: 31
<212> TYPE: PRT
<213> ORGANISM: Artificial Sequence
<220> FEATURE:
<223> OTHER INFORMATION: soluble chimeric peptide IQN17, shortened
      version #3
<220> FEATURE:
```

```
<221> NAME/KEY: ACETYLATION
<222> LOCATION: 1
<220> FEATURE:
<221> NAME/KEY: AMIDATION
<222> LOCATION: 31

<400> SEQUENCE: 7

Lys Ile Lys Lys Ile Glu Asn Glu Ile Ala Arg Ile Lys Lys Leu Leu
1               5                   10                  15

Gln Leu Thr Val Trp Gly Ile Lys Gln Leu Gln Ala Arg Ile Leu
            20                  25                  30

<210> SEQ ID NO 8
<211> LENGTH: 38
<212> TYPE: PRT
<213> ORGANISM: Artificial Sequence
<220> FEATURE:
<223> OTHER INFORMATION: soluble chimeric peptide IQN17, shortened
      version #4
<220> FEATURE:
<221> NAME/KEY: ACETYLATION
<222> LOCATION: 1
<220> FEATURE:
<221> NAME/KEY: AMIDATION
<222> LOCATION: 38

<400> SEQUENCE: 8

Lys Ile Glu Glu Ile Glu Ser Lys Gln Lys Lys Ile Glu Asn Glu Ile
1               5                   10                  15

Ala Arg Ile Lys Lys Leu Leu Gln Leu Thr Val Trp Gly Ile Lys Gln
            20                  25                  30

Leu Gln Ala Arg Ile Leu
        35

<210> SEQ ID NO 9
<211> LENGTH: 38
<212> TYPE: PRT
<213> ORGANISM: Artificial Sequence
<220> FEATURE:
<223> OTHER INFORMATION: soluble chimeric peptide IQN17, shortened
      version #5
<220> FEATURE:
<221> NAME/KEY: ACETYLATION
<222> LOCATION: 1
<220> FEATURE:
<221> NAME/KEY: AMIDATION
<222> LOCATION: 38

<400> SEQUENCE: 9

Lys Ile Glu Glu Ile Glu Ser Lys Ile Lys Lys Ile Glu Asn Glu Ile
1               5                   10                  15

Ala Arg Ile Lys Lys Leu Leu Gln Leu Thr Val Trp Gly Ile Lys Gln
            20                  25                  30

Leu Gln Ala Arg Ile Leu
        35

<210> SEQ ID NO 10
<211> LENGTH: 34
<212> TYPE: PRT
<213> ORGANISM: Artificial Sequence
<220> FEATURE:
<223> OTHER INFORMATION: designed trimeric coiled peptide GCN4-pIQI'
<220> FEATURE:
<221> NAME/KEY: ACETYLATION
<222> LOCATION: 1
<220> FEATURE:
<221> NAME/KEY: AMIDATION
<222> LOCATION: 34
```

-continued

```
<400> SEQUENCE: 10

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Ile Gly Glu
            20                  25                  30

Arg Tyr

<210> SEQ ID NO 11
<211> LENGTH: 31
<212> TYPE: PRT
<213> ORGANISM: Artificial Sequence
<220> FEATURE:
<223> OTHER INFORMATION: designed trimeric coiled coil peptide, IZ
<220> FEATURE:
<221> NAME/KEY: ACETYLATION
<222> LOCATION: 1
<220> FEATURE:
<221> NAME/KEY: AMIDATION
<222> LOCATION: 31

<400> SEQUENCE: 11

Tyr Gly Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Ile Glu Ala
            20                  25                  30

<210> SEQ ID NO 12
<211> LENGTH: 43
<212> TYPE: PRT
<213> ORGANISM: Artificial Sequence
<220> FEATURE:
<223> OTHER INFORMATION: region of gp41

<400> SEQUENCE: 12

Val Gln Ala Arg Gln Leu Leu Ser Gly Ile Val Gln Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu
        35                  40

<210> SEQ ID NO 13
<211> LENGTH: 56
<212> TYPE: PRT
<213> ORGANISM: Artificial Sequence
<220> FEATURE:
<223> OTHER INFORMATION: soluble chimeric peptide, IQN26
<220> FEATURE:
<221> NAME/KEY: ACETYLATION
<222> LOCATION: 1
<220> FEATURE:
<221> NAME/KEY: AMIDATION
<222> LOCATION: 56

<400> SEQUENCE: 13

Arg Met Lys Gln Ile Glu Asp Lys Ile Glu Glu Ile Glu Ser Lys Gln
1               5                   10                  15

Tyr Lys Ile Glu Asn Glu Ile Ala Arg Ile Lys Lys Leu Ile Val Gln
            20                  25                  30

Ala Arg Gln Leu Leu Ser Gly Ile Val Gln Gln Gln Asn Asn Leu Leu
        35                  40                  45

Arg Ala Ile Glu Ala Gln Gln His
    50                  55
```

```
<210> SEQ ID NO 14
<211> LENGTH: 55
<212> TYPE: PRT
<213> ORGANISM: Artificial Sequence
<220> FEATURE:
<223> OTHER INFORMATION: soluble chimeric peptide, IZN26
<220> FEATURE:
<221> NAME/KEY: ACETYLATION
<222> LOCATION: 1
<220> FEATURE:
<221> NAME/KEY: AMIDATION
<222> LOCATION: 55

<400> SEQUENCE: 14

Tyr Gly Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Ile Val Gln Ala
            20                  25                  30

Arg Gln Leu Leu Ser Gly Ile Val Gln Gln Gln Asn Asn Leu Leu Arg
        35                  40                  45

Ala Ile Glu Ala Gln Gln His
    50                  55

<210> SEQ ID NO 15
<211> LENGTH: 33
<212> TYPE: PRT
<213> ORGANISM: Artificial Sequence
<220> FEATURE:
<223> OTHER INFORMATION: designed trimeric coiled coil peptide,
      GCN4-pIQI
<220> FEATURE:
<221> NAME/KEY: ACETYLATION
<222> LOCATION: 1
<220> FEATURE:
<221> NAME/KEY: AMIDATION
<222> LOCATION: 33

<400> SEQUENCE: 15

Arg Met Lys Gln Ile Glu Asp Lys Ile Glu Glu Ile Leu Ser Lys Gln
1               5                   10                  15

Tyr His Ile Glu Asn Glu Ile Ala Arg Ile Lys Lys Leu Ile Gly Glu
            20                  25                  30

Arg

<210> SEQ ID NO 16
<211> LENGTH: 31
<212> TYPE: PRT
<213> ORGANISM: Artificial Sequence
<220> FEATURE:
<223> OTHER INFORMATION: designed trimeric coiled coil peptide,
      isoleucine zipper
<220> FEATURE:
<221> NAME/KEY: ACETYLATION
<222> LOCATION: 1
<220> FEATURE:
<221> NAME/KEY: AMIDATION
<222> LOCATION: 31

<400> SEQUENCE: 16

Tyr Gly Gly Ile Glu Lys Lys Ile Glu Ala Ile Glu Lys Lys Ile Glu
1               5                   10                  15

Ala Ile Glu Lys Lys Ile Glu Ala Ile Glu Lys Lys Ile Glu Ala
            20                  25                  30

<210> SEQ ID NO 17
```

-continued

```
<211> LENGTH: 32
<212> TYPE: PRT
<213> ORGANISM: Artificial Sequence
<220> FEATURE:
<223> OTHER INFORMATION: designed trimeric coiled coil peptide,
      GCN4-pIqI
<220> FEATURE:
<221> NAME/KEY: ACETYLATION
<222> LOCATION: 1

<400> SEQUENCE: 17

Met Lys Gln Ile Glu Asp Lys Ile Glu Glu Ile Leu Ser Lys Gln Tyr
1               5                   10                  15

His Ile Glu Asn Glu Ile Ala Arg Ile Lys Lys Leu Ile Gly Glu Arg
            20                  25                  30

<210> SEQ ID NO 18
<211> LENGTH: 17
<212> TYPE: PRT
<213> ORGANISM: Artificial Sequence
<220> FEATURE:
<223> OTHER INFORMATION: peptide, portion of HIV gp41 sequence

<400> SEQUENCE: 18

Leu Leu Gln Leu Thr Val Trp Gly Ile Lys Gln Leu Gln Ala Arg Ile
1               5                   10                  15

Leu

<210> SEQ ID NO 19
<211> LENGTH: 8
<212> TYPE: PRT
<213> ORGANISM: Artificial Sequence
<220> FEATURE:
<223> OTHER INFORMATION: 8 amino acid residues of GCN4-pIQI in shortened
      IQN17 #1

<400> SEQUENCE: 19

Glu Ile Ala Arg Ile Lys Lys Leu
1               5

<210> SEQ ID NO 20
<211> LENGTH: 15
<212> TYPE: PRT
<213> ORGANISM: Artificial Sequence
<220> FEATURE:
<223> OTHER INFORMATION: 15 amino acid residues of GCN4-pIQI in
      shortened IQN17 #2

<400> SEQUENCE: 20

Lys Gln Lys Lys Ile Glu Asn Glu Ile Ala Ala Ile Lys Lys Leu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: 15 amino acid residues of GCN4-pIQI in
      shortened IQN17 #3

<400> SEQUENCE: 21

Lys Ile Lys Lys Ile Glu Asn Glu Ile Ala Arg Ile Lys Lys Leu
1               5                   10                  15

<210> SEQ ID NO 22
<211> LENGTH: 22
<212> TYPE: PRT
```

```
<213> ORGANISM: Artificial Sequence
<220> FEATURE:
<223> OTHER INFORMATION: 21 amino acid residues of GCN4-pIQp in
      shortened IQN17 #4 plus one additional amino acid

<400> SEQUENCE: 22

Lys Ile Glu Glu Ile Glu Ser Lys Gln Lys Lys Ile Glu Asn Glu Ile
 1               5                  10                  15

Ala Arg Ile Lys Lys Leu
            20

<210> SEQ ID NO 23
<211> LENGTH: 21
<212> TYPE: PRT
<213> ORGANISM: Artificial Sequence
<220> FEATURE:
<223> OTHER INFORMATION: 21 amino acid residues of GCN4-pIQI in
      shortened IQN17 #5

<400> SEQUENCE: 23

Lys Ile Glu Glu Ile Glu Ser Lys Ile Lys Lys Ile Glu Asn Glu Ile
 1               5                  10                  15

Ala Arg Ile Lys Lys
            20

<210> SEQ ID NO 24
<211> LENGTH: 30
<212> TYPE: PRT
<213> ORGANISM: Artificial Sequence
<220> FEATURE:
<223> OTHER INFORMATION: GCN4-pIQI component of IQN36
<220> FEATURE:
<221> NAME/KEY: ACETYLATION
<222> LOCATION: 1

<400> SEQUENCE: 24

Arg Met Lys Gln Ile Glu Asp Lys Ile Glu Glu Ile Glu Ser Lys Gln
 1               5                  10                  15

Lys Lys Ile Glu Asn Glu Ile Ala Arg Ile Lys Lys Leu Ile
            20                  25                  30

<210> SEQ ID NO 25
<211> LENGTH: 36
<212> TYPE: PRT
<213> ORGANISM: Artificial Sequence
<220> FEATURE:
<223> OTHER INFORMATION: HIV amino acid residues of IQN36
<220> FEATURE:
<221> NAME/KEY: AMIDATION
<222> LOCATION: 36

<400> SEQUENCE: 25

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu
        35

<210> SEQ ID NO 26
<211> LENGTH: 17
<212> TYPE: PRT
<213> ORGANISM: Artificial Sequence
<220> FEATURE:
<223> OTHER INFORMATION: portion of HIV-2 sequence
```

```
<400> SEQUENCE: 26

Leu Leu Arg Leu Thr Val Trp Gly Thr Lys Asn Leu Gln Ala Arg Val
 1               5                  10                  15

Thr

<210> SEQ ID NO 27
<211> LENGTH: 17
<212> TYPE: PRT
<213> ORGANISM: Artificial Sequence
<220> FEATURE:
<223> OTHER INFORMATION: portion of SIV sequence

<400> SEQUENCE: 27

Leu Leu Arg Leu Thr Val Trp Gly Thr Lys Asn Leu Gln Thr Arg Val
 1               5                  10                  15

Thr

<210> SEQ ID NO 28
<211> LENGTH: 17
<212> TYPE: PRT
<213> ORGANISM: Artificial Sequence
<220> FEATURE:
<223> OTHER INFORMATION: peptide comprising invariant residues in HIV-1,
      HIV-2 and SIV
<220> FEATURE:
<221> NAME/KEY: VARIANT
<222> LOCATION: 3, 9, 11, 14, 16, 17
<223> OTHER INFORMATION: Xaa = any amino acid

<400> SEQUENCE: 28

Leu Leu Xaa Leu Thr Val Trp Gly Xaa Lys Xaa Leu Gln Xaa Arg Xaa
 1               5                  10                  15

Xaa

<210> SEQ ID NO 29
<211> LENGTH: 24
<212> TYPE: PRT
<213> ORGANISM: Artificial Sequence
<220> FEATURE:
<223> OTHER INFORMATION: 24 residues from N-terminal end of N36

<400> SEQUENCE: 29

Ser Gly Ile Val Gln Gln Gln Asn Asn Leu Leu Arg Ala Ile Glu Ala
 1               5                  10                  15

Gln Gln His Leu Leu Gln Leu Thr
            20

<210> SEQ ID NO 30
<211> LENGTH: 55
<212> TYPE: PRT
<213> ORGANISM: Artificial Sequence
<220> FEATURE:
<223> OTHER INFORMATION: IQN24n

<400> SEQUENCE: 30

Met Arg Met Lys Gln Ile Glu Asp Lys Ile Glu Glu Ile Glu Ser Lys
 1               5                  10                  15

Gln Lys Lys Ile Glu Asn Glu Ile Ala Arg Ile Lys Lys Leu Ile Ser
                20                  25                  30

Gly Ile Val Gln Gln Gln Asn Asn Leu Leu Arg Ala Ile Glu Ala Gln
            35                  40                  45

Gln His Leu Leu Gln Leu Thr
        50                  55
```

<210> SEQ ID NO 31
<211> LENGTH: 41
<212> TYPE: PRT
<213> ORGANISM: Artificial Sequence
<220> FEATURE:
<223> OTHER INFORMATION: peptide IZN17
<220> FEATURE:
<221> NAME/KEY: ACETYLATION
<222> LOCATION: 1
<220> FEATURE:
<221> NAME/KEY: AMIDATION
<222> LOCATION: 41

<400> SEQUENCE: 31

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Gln Leu Gln Ala Arg Ile Leu
        35                  40

<210> SEQ ID NO 32
<211> LENGTH: 48
<212> TYPE: PRT
<213> ORGANISM: Artificial Sequence
<220> FEATURE:
<223> OTHER INFORMATION: peptide IZN23
<220> FEATURE:
<221> NAME/KEY: ACETYLATION
<222> LOCATION: 1
<220> FEATURE:
<221> NAME/KEY: AMIDATION
<222> LOCATION: 48

<400> SEQUENCE: 32

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Ala Gln Gln His Leu
            20                  25                  30

Leu Gln Leu Thr Val Trp Gly Ile Lys Gln Leu Gln Ala Arg Ile Leu
        35                  40                  45

<210> SEQ ID NO 33
<211> LENGTH: 62
<212> TYPE: PRT
<213> ORGANISM: Artificial Sequence
<220> FEATURE:
<223> OTHER INFORMATION: peptide IZN26
<220> FEATURE:
<221> NAME/KEY: ACETYLATION
<222> LOCATION: 1
<220> FEATURE:
<221> NAME/KEY: AMIDATION
<222> LOCATION: 62

<400> SEQUENCE: 33

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Ser Gly Ile Val Gln Gln
            20                  25                  30

Gln Asn Asn Leu Leu Arg Ala Ile Glu Ala Gln Gln His Leu Leu Gln
        35                  40                  45

Leu Thr Val Trp Gly Ile Lys Gln Leu Gln Ala Arg Ile Leu
    50                  55                  60

```
<210> SEQ ID NO 34
<211> LENGTH: 22
<212> TYPE: PRT
<213> ORGANISM: Artificial Sequence
<220> FEATURE:
<223> OTHER INFORMATION: peptide N23

<400> SEQUENCE: 34

Glu Ala Gln Gln His Leu Leu Gln Leu Thr Val Trp Gly Ile Lys Gln
 1               5                  10                  15

Leu Gln Ala Arg Ile Leu
            20

<210> SEQ ID NO 35
<211> LENGTH: 36
<212> TYPE: PRT
<213> ORGANISM: Artificial Sequence
<220> FEATURE:
<223> OTHER INFORMATION: peptide N36

<400> SEQUENCE: 35

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu
        35

<210> SEQ ID NO 36
<211> LENGTH: 26
<212> TYPE: PRT
<213> ORGANISM: Artificial Sequence
<220> FEATURE:
<223> OTHER INFORMATION: peptide N26

<400> SEQUENCE: 36

Val Gln Ala Arg Gln Leu Leu Ser Gly Ile Val Gln Gln Gln Asn Asn
 1               5                  10                  15

Leu Leu Arg Ala Ile Glu Ala Gln Gln His
            20                  25
```

SOLUBLE CHIMERIC PEPTIDE INHIBITORS OF HIV ENTRY COMPRISING AN IZ TRIMERIC COILED-COIL PEPTIDE AND HIV GP41 N-HELIX COILED-COIL PEPTIDE

RELATED APPLICATIONS

This application is a continuation of U.S. application Ser. No. 10/395,817, filed Mar. 21, 2003, now U.S. Pat. No. 7,226,598 which is a continuation of International Application No. PCT/US01/29637, which designated the United States and was filed Sep. 21, 2001, published in English, which is a continuation of U.S. application Ser. No. 09/668,072, filed Sep. 22, 2000 now U.S. Pat. No. 6,747,126 which is a continuation-in-part of U.S. application Ser. No. 09/364,497, filed Jul. 30, 1999, now U.S. Pat. No. 6,818,740 and which claims the benefit of U.S. Provisional Application No. 60/132,295, filed May 3, 1999, U.S. Provisional Application No. 60/101,058, filed Sep. 18, 1998, U.S. Provisional Application No. 60/100,265, filed Sep. 14, 1998, and U.S. Provisional Application No. 60/094,676, filed Jul. 30, 1998.

U.S. application Ser. No. 10/395,817 is also a continuation of U.S. application Ser. No. 09/746,742, filed on Dec. 21, 2000, now U.S. Pat. No. 6,841,657 which is a continuation of International Application No. PCT/US99/17351, which designated the United States and was filed Jul. 30, 1999, published in English, and which claims the benefit of U.S. Provisional Application No. 60/132,295, filed May 3, 1999, U.S. Provisional Application No. 60/101,058, filed Sep. 18, 1998, U.S. Provisional Application No. 60/100,265, filed Sep. 14, 1998, and U.S. Provisional Application No. 60/094,676, filed Jul. 30, 1998.

U.S. application Ser. No. 10/395,817 is also a continuation of U.S. application Ser. No. 09/668,072, filed Sep. 22, 2000, now U.S. Pat. No. 6,747,126 which is a continuation-in-part of U.S. application Ser. No. 09/364,497, filed Jul. 30, 1999, now U.S. Pat. No. 6,818,740 and which claims the benefit of U.S. Provisional Application No. 60/132,295, filed May 3, 1999, U.S. Provisional Application No. 60/101,058, filed Sep. 18, 1998, U.S. Provisional Application No. 60/100,265, filed Sep. 14, 1998, and U.S. Provisional Application No. 60/094,676, filed Jul. 30, 1998.

U.S. application Ser. No. 10/395,817 is also a continuation of U.S. application Ser. No. 09/364,497, filed Jul. 30, 1999, now U.S. Pat. No. 6,818,740 which claims the benefit of U.S. Provisional Application No. 60/132,295, filed May 3, 1999, U.S. Provisional Application No. 60/101,058, filed Sep. 18, 1998, U.S. Provisional Application No. 60/100,265, filed Sep. 14, 1998, and U.S. Provisional Application No. 60/094,676, filed Jul. 30, 1998.

The entire teachings of all of the above-referenced applications are incorporated herein by reference.

GOVERNMENT SUPPORT

Work described herein was funded, in whole or in part, by Grant Number P01 GM56552 from the National Institutes of Health. The United States Government has rights in the invention.

BACKGROUND OF THE INVENTION

HIV is the virus that is responsible for the worldwide AIDS epidemic. The initial stages of HIV infection involve the fusion of viral membrane with the target cell membrane, a process that injects the viral contents into the cellular cytoplasm. On the viral side, the molecular complex responsible for the fusion activity contains the surface protein gp120 and the transmembrane protein gp41. It is the current hypothesis that gp120 interacts with the proteins CD4 and coreceptor on the target cell, resulting in a conformational change that causes gp41 to insert its amino terminus (fusion peptide region) into the target cell membrane. This structural rearrangement promotes the fusion of virus and cellular membranes through a poorly understood mechanism.

SUMMARY OF THE INVENTION

Described herein are chimeric peptides comprising a soluble trimeric coiled-coil and all or a portion of the N-peptide region of HIV gp41. These molecules are stable, trimeric coiled-coils that inhibit HIV entry into cells, such as human cells. Such peptides can be further assessed to demonstrate their ability to serve as potent anti-HIV therapeutic molecules and thus, as therapeutic molecules or drugs.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2 is the amino acid sequences of IQ peptides (SEQ ID Nos: 1-9).

FIGS. 4A-4E are photographs of results of syncytia assays carried out in the absence of IQN peptide (FIG. 4A), in the presence of IQN17 at 80 nM (FIG. 4B) or at 320 nM (FIG. 4C) or in the presence of IQN23 at 80 nM (FIG. 4D) or at 320 nM (FIG. 4E).

FIG. 10 is the amino acid sequence of IQN26 (SEQ ID NO: 13).

FIG. 11 is the amino acid sequence of IZN26 (SEQ ID NO: 14).

DETAILED DESCRIPTION OF THE INVENTION

Figure 1:
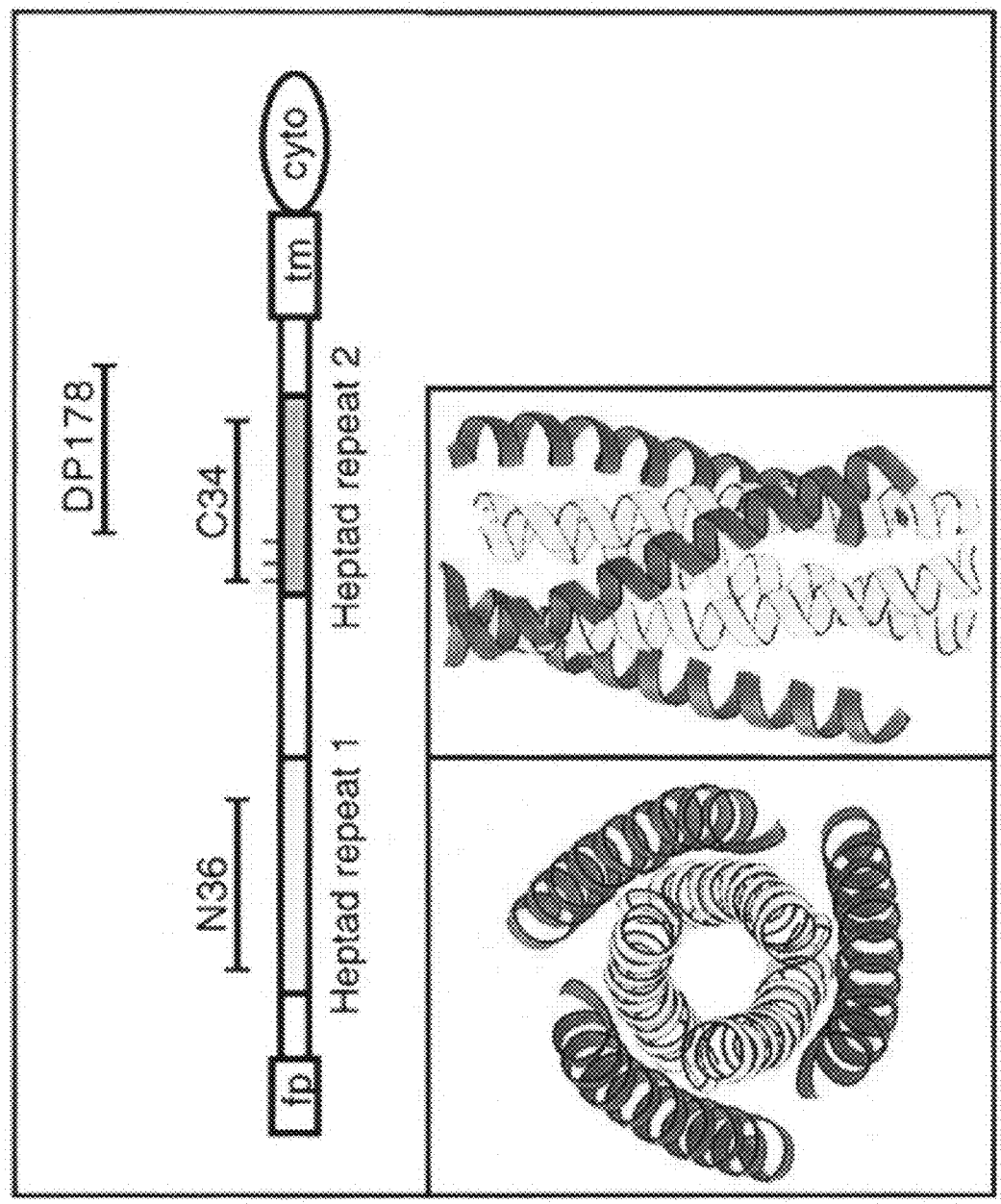
FIG. 1 is the structural arrangement of HIV gp41. Helical regions (heptad repeats) are shown in grey and the relative position of N—(N36) and C—(C34, DP 178) peptides are indicated. In the ribbon diagram of the helical region, the N-peptides are in light grey and the C-peptides are in dark grey.
Figure 3A:
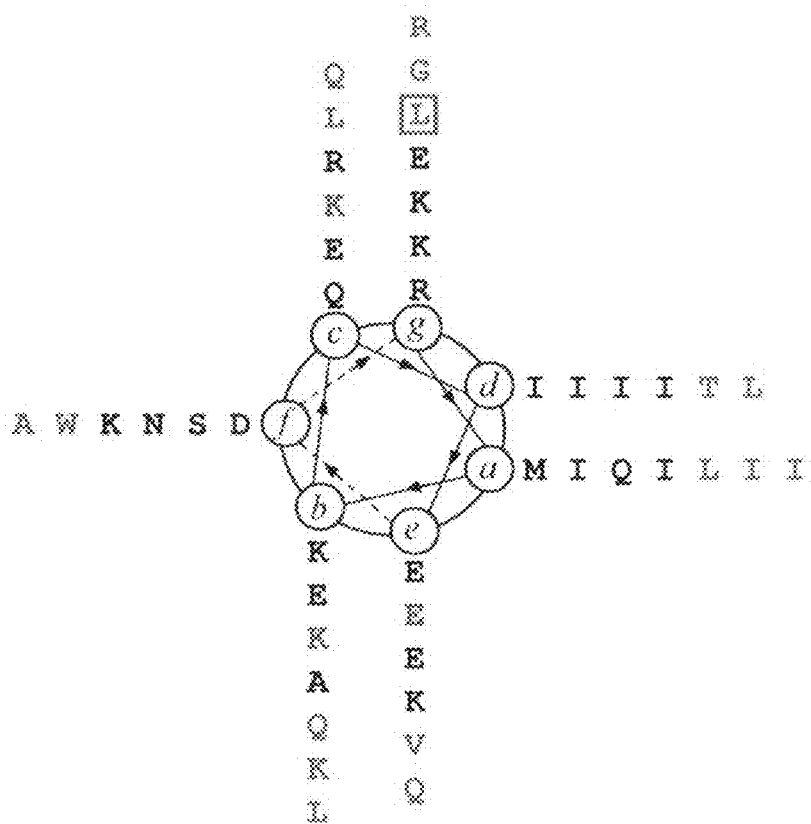
FIGS. 3A-3C show, respectively, a helical wheel representation of IQN17 (FIG. 3A); the CD spectrum of IQN17 (FIG. 3B); and analytical ultracentrifugation data for IQN17 (FIG. 3C). "XLA" is referred to herein as analytical ultracentrifugation.
Figure 3B:
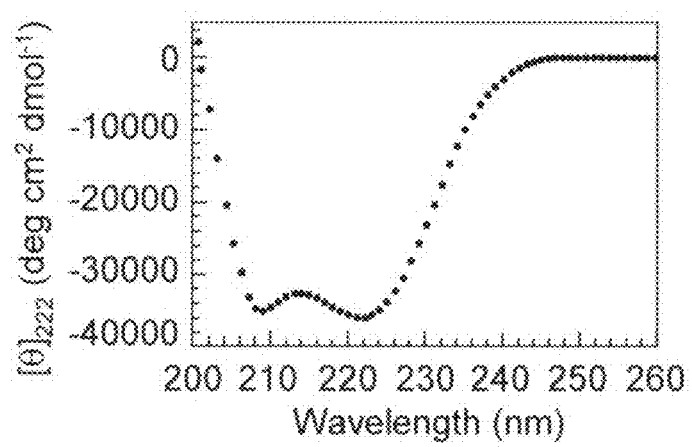
Figure 3C:
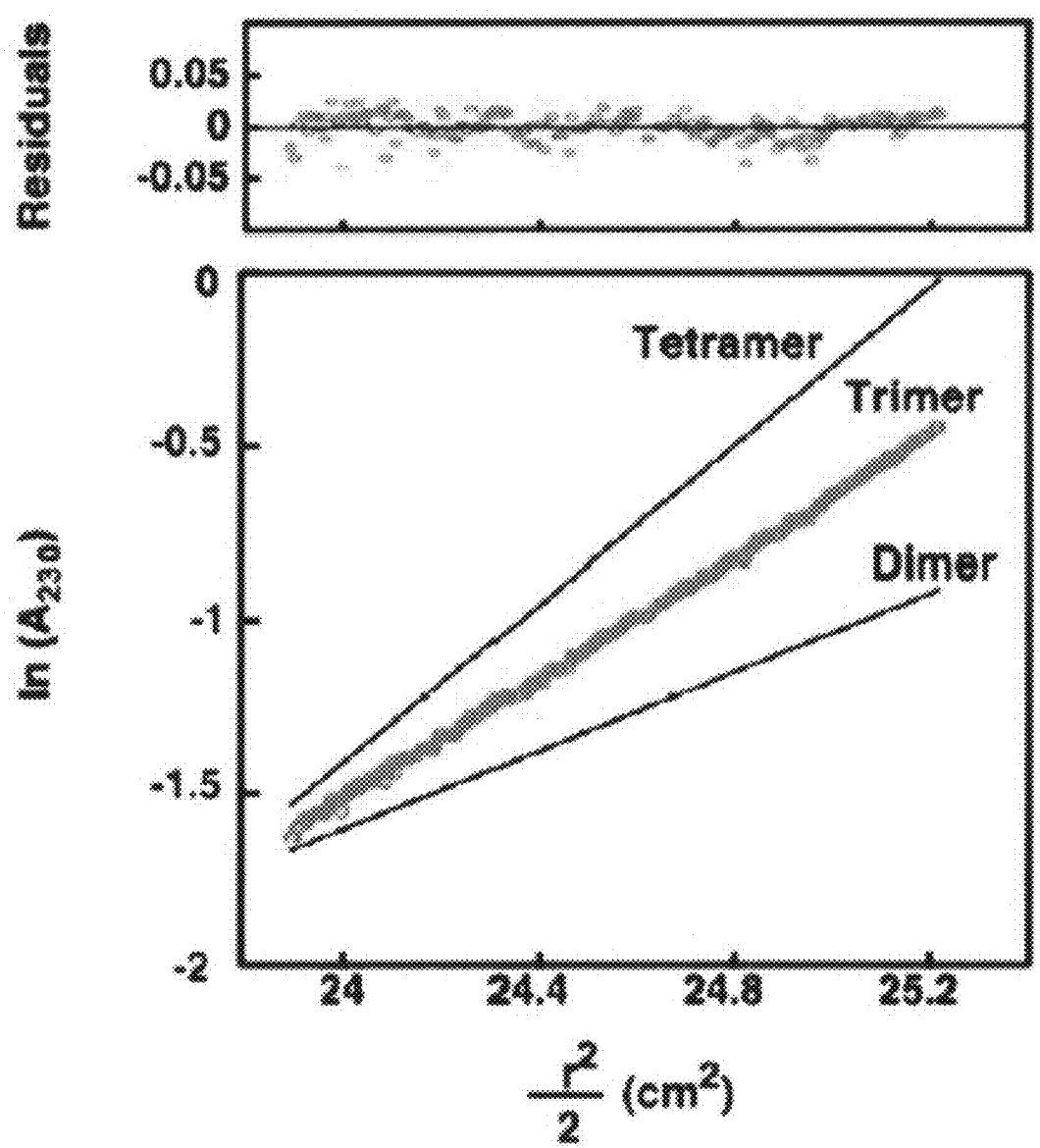
Figure 5:
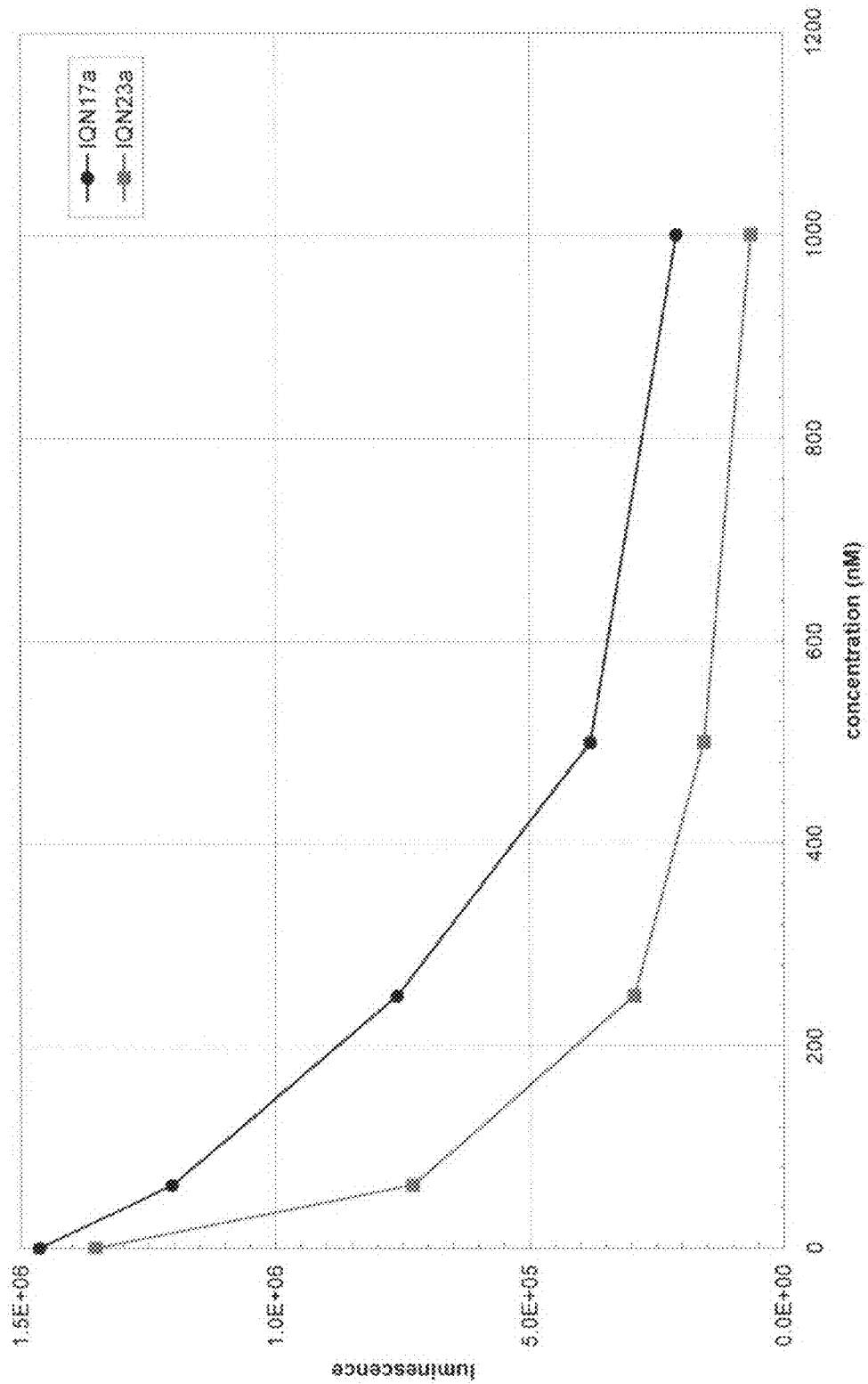
FIG. 5 is a graphic representation of the inhibitory activity of IQN17 and IQN23 in a viral infectivity assay.
Figure 6:
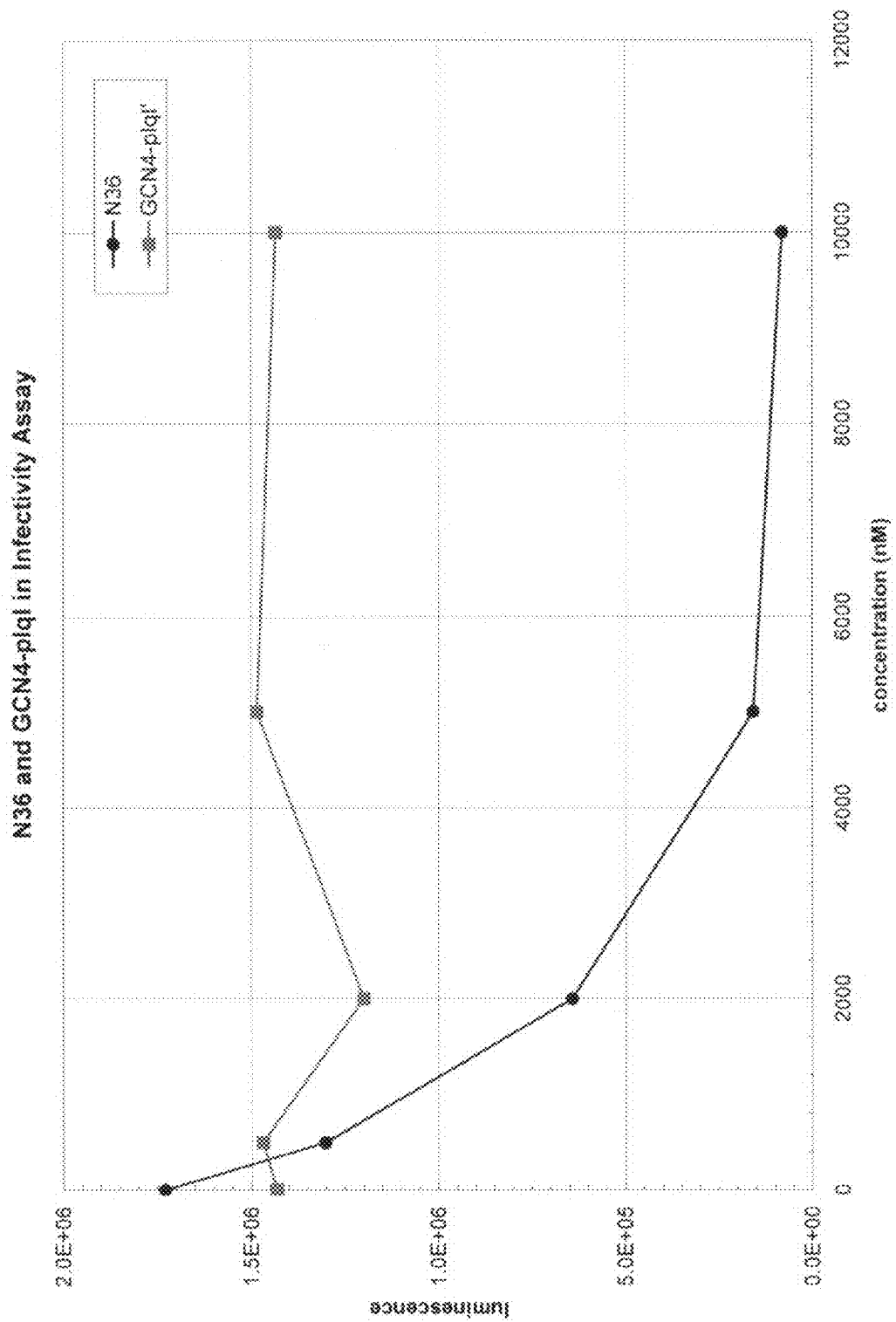
FIG. 6 is a graphic representation of the inhibitory activity of N36 and GCN4-pI$_Q$I in a viral infectivity assay. The results presented clearly show a lack of inhibitory activity by both N36 and GCN-pI$_Q$I.
Figure 7:
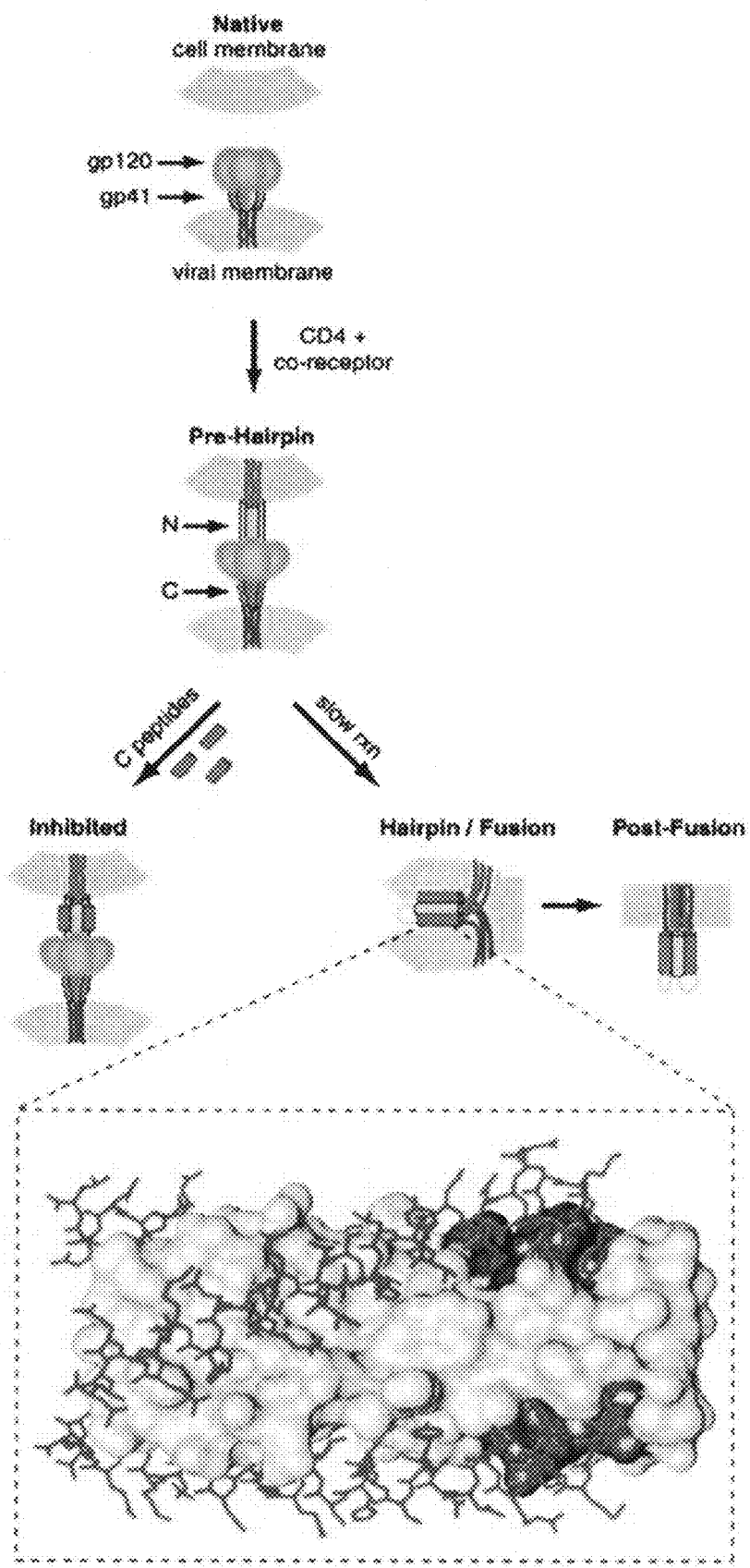
FIG. 7 is a working model for HIV membrane fusion (Chan & Kim 1988). In the native state of HIV-1 env ("Native"), the fusion-peptide and N-peptide regions of gp41 are not exposed. Following interaction with cellular receptors (CD4 and co-receptor), a conformational change results in formation of the transient pre-hairpin intermediate ("Pre-hairpin"), in which the fusion-peptide regions (red lines) are inserted into the cell membrane and the coiled coil of the N-peptide region of gp41 (indicated as "N") is exposed. However, the C-peptide region of gp41 (indicated as "C") is constrained and unavailable for interaction with the coiled coil. Thus, exogenous C-peptides can bind to the pre-hairpin intermediate and inhibit fusion in a dominant-negative manner ("Inhibited"). In the absence of inhibitors, the pre-hairpin intermediate resolves to the hairpin structure and membrane fusion results ("Hairpin/Fusion"), although it is not known if hairpin formation precedes membrane fusion per se. The inset depicts the 2.0 Å X-ray crystal structure of N36/C34, a peptide version of the HIV-1 gp41 core (Chan et al. 1997). Three central N-peptides form a coiled coil, shown here as a surface representation, and three helical C-peptides pack along conserved grooves on the surface of the coiled coil trimer. There are three symmetry-related hydrophobic pockets on the surface of the N-peptide coiled coil (shaded).
Figure 8:
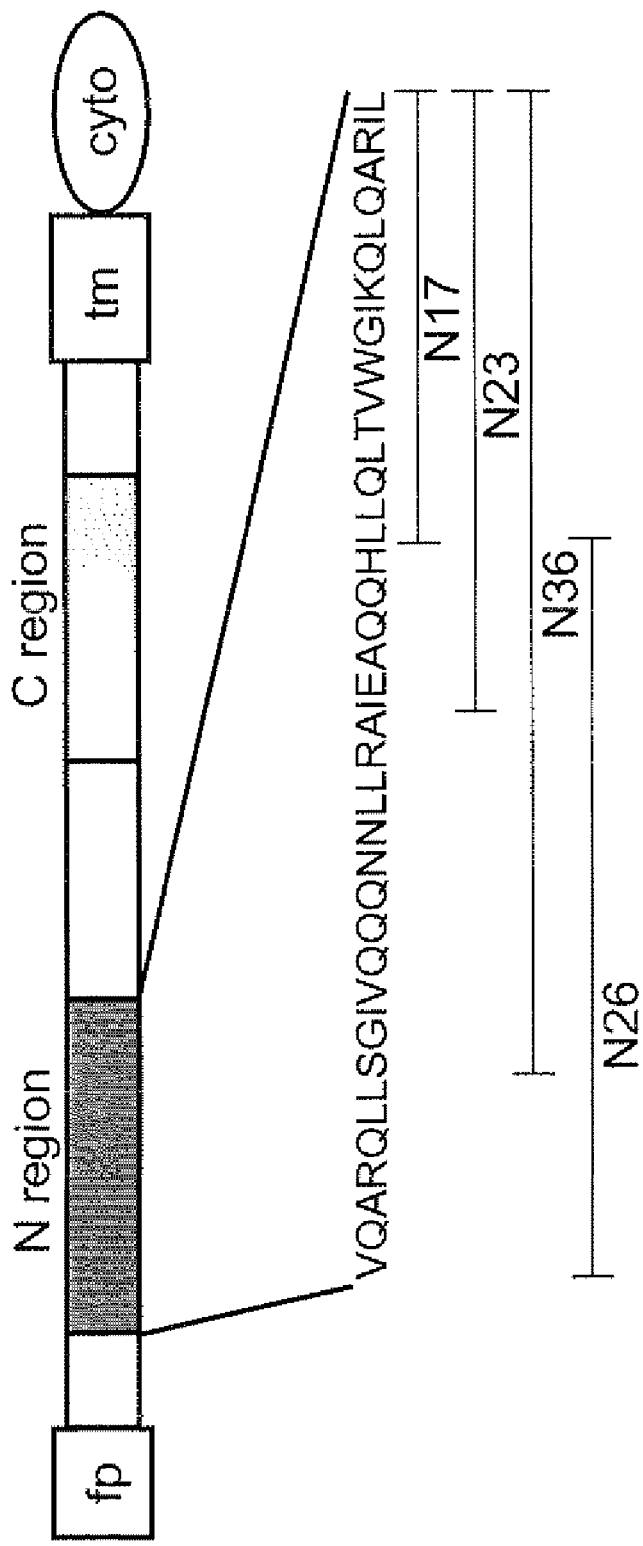
FIG. 8 is a graphic illustration showing that the chimeric peptides are composed of two parts: 1) one of the designed trimeric coiled-coils (GCN4-pI$_Q$I or IZ) (SEQ ID Nos: 10 and 11) and 2) one of the four regions of gp41 (SEQ ID NO: 12). These regions are designated N17 (SEQ ID NO: 18), N23 (SEQ ID NO: 34), N36 (SEQ ID NO: 35) and N26 (SEQ ID NO: 36).
Figure 9:
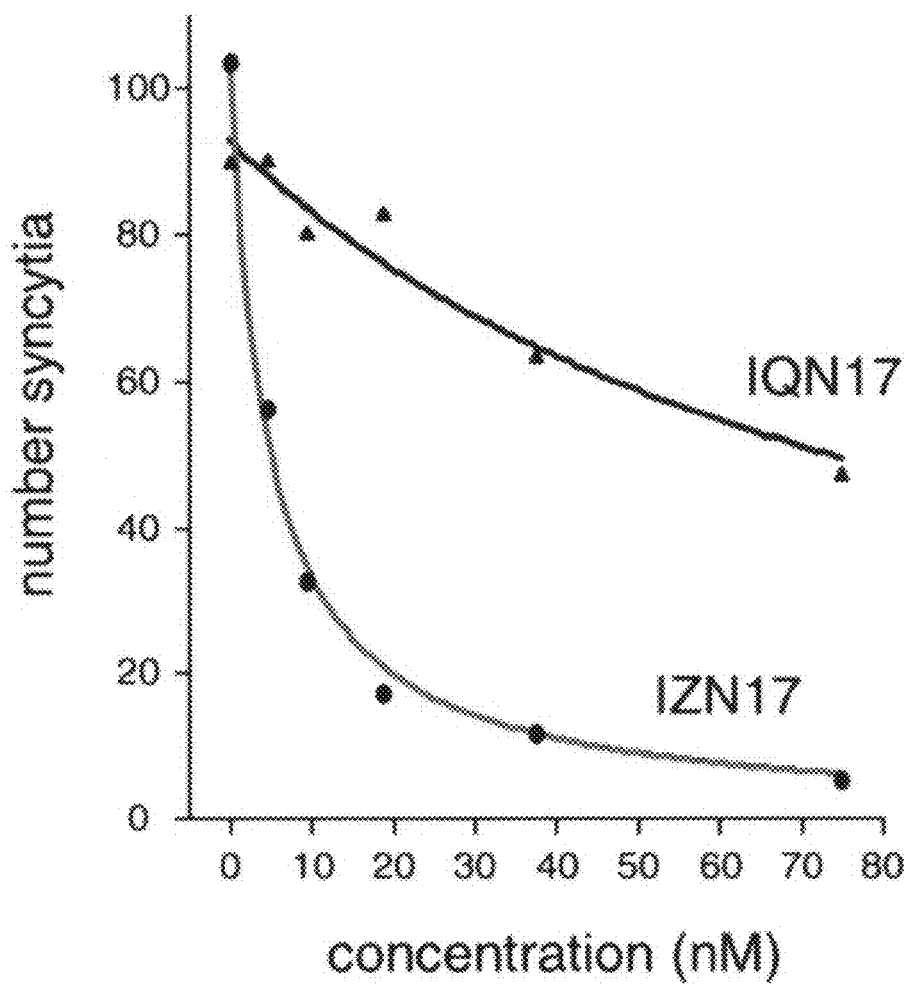
FIG. 9 is a graph of concentration (mM) versus number syncytium showing the results of the cell/cell fusion assay in the presence of IQN17 and IZN17.

The present invention relates to soluble peptides, referred to as soluble IQ (or IN) peptides, which, under the conditions described herein, fold into a stable trimeric coiled-coil (helical) structure and inhibit HIV infection of mammalian cells, such as human cells. In a specific embodiment, the soluble IQ peptides also bind D-peptide inhibitors of HIV infection of human cells, under the conditions described herein. In one embodiment, soluble IQ peptides comprise a trimeric coiled-coil peptide and a portion of the N-helix coiled-coil of HIV gp41 (HIV gp41 N-peptide); the components are present in the following "order": N-terminus-trimeric coiled-coil peptide-☐ N-helix coiled coil of HIV gp41-C-terminus. The trimeric coiled-coil peptide can be from (comprise amino acid residues that correspond to those in) a variety of sources, such as GCN4, the yeast transcription activator; Moloney Murine Leukemia Virus (MoMLV); GCN4-pII, GCN4-pI$_Q$I and the ABC heterotrimer. It can also be from other designed trimeric coiled coils such as the isoleucine zipper (IZ) described by Tanaka et al., or derivatives of this 'IZ' sequence. In those embodiments in which the trimeric coiled-coil peptide is from the isoleucine zipper, they are referred to as IZ peptides. Alternatively, it can comprise a trimeric coiled-coil peptide from HIV. Three examples of coiled-coils of interest are:

```
GCN4-pIQI:
                                        (SEQ ID NO: 15)
Ac-RMKQIEDKIEEILSKQYHIENEIARIKKLIGER-NH2

GCN4-pIQI':
                                        (SEQ ID NO: 10)
Ac-RMKQIEDKIEEIESKQKKIENEIARIKKLIGERY-NH2

Tanaka's isoleucine zipper:
                                        (SEQ ID NO: 16)
Ac-YGGIEKKIEAIEKKIEAIEKKIEAIEKKIEA-NH2
```

The "IZ" molecule derived from Tanaka et al., but with mutations:

```
                                        (SEQ ID NO: 11)
Ac-YGGIKKEIEAIKKEQEAIKKKIEAIEKEIEA-NH2.
```

The amino acid residues that comprise an IQ peptide of the present invention can be amino acid residues that are contiguous (consecutive) or noncontiguous (nonconsecutive) in the trimeric coiled-coil peptide from which it is derived and/or amino acid residues that are contiguous (consecutive) or non-contiguous (nonconsecutive) in HIV gp41 N-peptide, provided that the resulting IQ peptide (the IQ peptide in which they are present) is stable, soluble, helical, and trimeric and inhibits HIV infection of human cells. In the embodiments of IQ peptides in which nonconsecutive amino acid residues of either or both components of the IQ peptide are present, the residues, as included in the IQ peptide, can be consecutive or can be separated or joined by a linker. The linker can be, for example, an amino acid residue(s) that do not occur between two amino acid residues in the peptide from which the component is derived. Alternatively, the "linker" can be a chemical or synthetic linker. A component of an IQ peptide of the present invention is considered to be "derived from" another peptide (e.g., a trimeric coiled-coil or HIV gp41 N-peptide) if the component itself (or the nucleic acid molecule(s) that encode the amino acid sequence) is obtained or isolated/separated from a source in which it occurs (e.g., from a cell in which the peptide occurs, such as a portion of a protein from which it can be removed) or is produced by recombinant DNA methods, chemical synthesis or any other method, to comprise an amino acid sequence or a nucleic acid sequence that is the same as or substantially the same as the sequences of the peptide. That is, the term is intended to be interpreted broadly and does not require that a component be physically derived from the peptide referred to.

In the embodiments in which the soluble IQ peptides comprise an IQ region that is a GCN4 trimeric coiled-coil peptide, they are referred to as IQN peptides. IQN peptides comprise all or a portion of GCN4-pI$_Q$I (formerly referred to as GCN4-pIQ in U.S. Provisional Application 60/101,058; Eckert D. M. et al. *J. Mol. Biol.*, 284: 859-865 (1998)) or a modified version of all or a portion of GCN4-pI$_Q$I, such as a modified portion that includes mutations for increased solubility, and all or a portion of the HIV gp41 N-peptide. Typically, 5 or more (e.g., 7, 8, 9 or 10) amino acid residues from HIV gp41 N-peptide up to and including all of the residues of the N-peptide will comprise the HIV gp41 component of the IQ peptides.

Soluble IQN peptides of the present invention comprise, in specific embodiments, a portion of the HIV gp41 N-peptide sufficient to bind the C-peptide (region) of HIV gp41 and a sufficient portion of the GCN4 trimeric coiled-coil peptide or a modified version of the GCN4 peptide that the resulting IQN peptide is a soluble trimeric (helical) coiled coil. In further embodiments, IQN peptides comprise a portion of the HIV gp41 N-peptide that includes the amino acid residues which form the pocket or cavity of HIV gp41 (the pocket-comprising residues of the N-peptide). In yet further embodiments, IQN peptides do not comprise amino acid residues which form the pocket or cavity of HIV gp41. They do, however, comprise amino acid residues from HIV gp41. (See, for example, IQN23, IQN36 and IQN26).

Nomenclature of IQ peptides refers to the number of amino acid residues from the HIV gp41 N-peptide or a modified version of HIV gp41 N-peptide present in the IQ peptide. For example, 17 amino acid residues of HIV gp41 are included in the IQN17 peptide described herein. As explained above, the trimeric coiled coil peptide component of an IQ peptide must be sufficient in amino acid composition (identity and number/length) to result, when joined to the HIV gp41 N-peptide portion, in formation of a soluble trimeric helical (coiled-coil) IQ peptide. In certain embodiments of the IQN peptides of the present invention, the trimeric coiled-coil peptide, referred to as the "GCN4 portion", comprises at least 15, 16, 17, 18, 19 or 20 amino acid residues of GCN4. The amino acid residues present in the components of an IQN peptide can correspond to amino acid residues that are contiguous (consecutive) or noncontiguous (nonconsecutive) in, respectively, the GCN4 transcription activator (or GCN4-pI$_Q$I) and HIV gp41 N-peptide or a modified version of the activator or the N-peptide, provided that the resulting IQN peptide is an inhibitor of HIV infection of human cells, as described herein. The IQ and IZ peptides of the present invention can be produced as a continuous peptide or as components that are joined or linked after they are formed. As used herein, the terms "joined" or "joined in such a manner" or "incorporated" include incorporating amino acid residues by either approach.

For example, the GCN component of an IQN peptide can comprise consecutive amino acid residues from GCN4-pI$_Q$I, modified, if desired (e.g., to increase solubility, as is the case in IQN17 (SEQ ID NO.: 1)). Alternatively, amino acid residues that are not consecutive in the GCN4 activator (or in GCN4-pI$_Q$I), joined in such a manner that they are nonconsecutive or consecutive in the resulting GCN4 component of an IQN peptide, can be incorporated in the IQN peptide. Similarly, the amino acid residues of the HIV gp41 N-peptide component of an IQN peptide of the present invention can be amino acid residues that occur consecutively or nonconsecutively in HIV gp41 N-peptide and can be incorporated into in IQN peptide in such a manner that they are consecutive or nonconsecutive in the resulting peptide. In the embodiments in which nonconsecutive amino acid residues are used, they can be separated by one or more "linker" molecules, if needed to retain the respective functions/characteristics of the components and of the IQN peptide. For example, an amino acid residue(s) other than the residue(s) that normally occur between two amino acid residues of GCN4 or HIV gp41 N-peptide can be used to link or join the two amino acid residues in the IQN peptide. Alternatively, the linker can be a chemical or synthetic linker, for example. Under the conditions described herein, IQN peptides have been shown to fold into a stable structure, bind peptide inhibitors of HIV-1 infection and inhibit HIV infection of human cells. For example, IQN17 and IQN23 have been shown to fold into stable structures, bind D-peptides previously shown to be inhibitors of HIV-1 infection and inhibit HIV infection of human cells. IQN36, as well as versions of IQN17 that are shortened in the 'IQ' region are also described. These shortened versions may be therapeutically advantageous because, for example, they are easier and less expensive to produce than are larger peptides.

A specific embodiment of an IQN peptide is IQN17, which contains 29 residues of GCN4-pI$_Q$I, including three mutations for increased solubility, and 17 residues of HIV; there is a one residue overlap between the two proteins, making the total length of the fusion protein 45 residues. The sequence of GCN4-pIqI is ac-MKQIEDKIEEILSKQYHIENE-IARIKKLIGER (SEQ ID NO: 17). In this embodiment, the HIV Sequence is: LLQLTVWG IKQLQARIL (SEQ ID NO: 18). The sequence of IQN17 is: ac-RMKQIEDKIEE-IESKQKKIENEIARIKK LLQLTVWGIKQLQARIL-am (SEQ ID NO.: 1). In the sequences presented, ac represents an N-terminal acetyl group and am represents a C-terminal amide group. IQN17 has been shown to inhibit HIV of human cells, as described herein.

Shortened versions of IQN17, which each contain 17 amino acid residues of HIV gp41 N-helix (SEQ ID NO.: 2), but include a shorter GCN component than is present in IQN17, are also the subject of this invention. Specific examples of these shortened IQN17 peptides are:

a) shortened IQN17 #1, (SEQ ID NO.: 5), in which there are eight amino acid residues of GCN4-pI$_Q$I: EIARIKKL (SEQ ID NO.: 19);
b) shortened IQN17 #2 (SEQ ID NO.: 6), in which there are 15 amino acid residues of GCN4-pI$_Q$I: KQKKIENE-IAAIKKL (SEQ ID NO.: 20) and
c) shortened IQN17 #3 (SEQ ID NO.: 7), in which there are 15 non-HIV amino acid residues KIKKIENEIARIKKL (SEQ ID NO.: 21). This is GCN4-pI$_Q$I' with an I to Q mutation, and is referred to as GCN4-pII'.
d) shortened IQN17 #4 (SEQ ID NO.: 8), in which there are 21 amino acid residues of GCN4-pIQp: KIEEIESKQK-KIENEIARIKKL (SEQ ID NO.: 22 and
e) shortened IQN17 #5 (SEQ ID NO.: 9), in which there are 21 non-HIV amino acid residues: KIEEIESKIKKIENE-IARIKK (SEQ ID NO.: 23).

Another specific embodiment of this invention is IQN23. One embodiment, referred to as IQN23 version 1, has the following sequence: ac-RMKQIEDKIEEILSKQYHIENE-IARIKKLIEAQQHLLQLTVWGIKQLQARIL-am (SEQ ID NO.: 2). In IQN23 version 1, there are 29 amino acid residues in the GCN4 component and 23 amino acid residues in the HIV gp41 component (a total of 52 amino acid residues). A second embodiment of an IQN23, referred to as IQN23 version 2, also includes 23 amino acid residues of N-peptide of gp41 and 29 amino acid residues in its GCN component, but differs from IQN23, version 1 at amino acid residues 17 and 18 (and the L at position 15 is changed to E). In version 1, these two residues are, respectively, Y and H and in version 2, they are, respectively, both K. Three modifications have been made—the L, Y and H. These are the same three modifications that were made to make IQN17 more soluble. The two "versions" are referred to as GCN4-pI$_Q$I and GCN4-pI$_Q$I'. The sequence of IQN23 version 2 is: ac-RMKQIEDKIEE-IESKQKKIENE-IARIKKLIEAQQHLLQLTVWGIKQLQARILNH2 SEQ ID NO.: 3). As described herein, IQN23 (both versions) inhibits HIV infection more effectively than does IQN17.

Another specific embodiment of IQN peptides of this invention is IQN36, in which there are 30 amino acid residues of GCN4-pI$_Q$I and 36 amino acid residues of HIV. The sequence of IQN36 (SEQ ID NO.: 4) is shown in FIG. 2. The sequence of the GCN4-pI$_Q$I component is: ac-RMKQIEDK-IEEIESKQKKIENEIARIKKLI (SEQ ID NO.: 24) and the HIV amino acid residues are:

(SEQ ID NO.: 25)
SGIVQQQNNLLRAIEAQQHLLQLTVWGIKQLQARIL-NH2.

The sequence of IQN36 is:
(SEQ ID NO.: 3)
ac-RMKQIEDKIEEIESKQKKIENEIARIKKLISGIVQQQNNLLRAIEAQ

QHLLQLTVWGIKQLQARIL-NH2.

A wide variety of fusion proteins which are variants of IQN17 can be produced and used to inhibit HIV. Fusion proteins include proteins made as a single continuous molecule or as components that are subsequently joined or linked together. Any of a wide variety of variations can be made in the GCN4-pIqI component of IQN17 and used in the method, provided that these changes do not alter the trimeric state of the coiled-coil. For example, the amino acid composition of the GCN4 component can be changed by the addition, substitution, modification and/or deletion of one or more amino acid residues, provided that the trimeric state of the coiled-coil is maintained. For example, the Asp residue in IQN17 (at an "f-position" of the coiled coil) can be replaced by any of the naturally-occurring amino acids. (O'Neil and DeGrado, Science 250:646 (1990)). Alternatively, this component of the fusion protein can be a trimenic version of the coiled-coil region of another protein, such as that from Moloney Murine Leukemia Virus (Fass, D. et al. Nature Struct. Biology, 3:465 (1996)), GCN4-pII (Harbury et al., Nature, 317:80, 1994) or the ABC heterotrimer (Nautiyal and Alber, Protein Science 8:84 (1999)), or the isoleucine zipper described by Tanaka, et al.

Changes can also be made in the amino acid composition of the fusion protein component which is the C-terminal portion of the HIV gp41 N peptide to produce a variety of fusion proteins to be used to prevent HIV infection of cells. The C-terminal portion can be changed by the addition, substitution, modification and/or deletion of one or more amino acid residues. The amino acid composition of either or both components of the fusion protein can be altered, and there is no limit to the number or types of amino acid residue changes possible, provided that the trimeric state of the coiled-coil is maintained. It is not necessary that the pocket or cavity of gp41 be included, although in many embodiments the pocket is present.

In all embodiments, controlled or time release (gradual release, release at a particular time after administration or insertion) of the drug can be effected by, for example, incorporating the drug into a composition which releases the drug gradually or after a defined period of time. Alternatively, the drug can be incorporated into a composition which releases the drug immediately or soon after its administration or application (e.g., into the blood, vagina, mouth or rectum). Combined release (e.g., release of some of the drug immediately or soon after insertion, and over time or at a particular time after insertion) can also be effective (e.g., by producing a composition which is comprised of two or more materials: one from which release or delivery occurs immediately or soon after insertion and/or one from which release or delivery is gradual and/or one from which release occurs after a specified period). For example, a drug or drugs which bind the HIV cavity can be incorporated into a sustained release composition such as that taught in U.S. Pat. No. 4,707,362. The cream, foam, gel or suppository can be one also used for birth control purposes (e.g., containing a spermicide or other contraceptive agent), although that is not necessary (e. a., it can be used solely to deliver the anti-HIV drug, alone or in combination with another non-contraceptive agent, such as an antibacterial or antifungal drug or a lubricating agent). An anti-HIV drug of the present invention can also be administered to an individual through the use of a contraceptive device (e.g., condom, cervical cap, diaphragm) which is coated with or has incorporated therein in a manner which permits release under conditions of use a drug or drugs which bind the HIV gp41 N-helix coiled coil. Release of the drug(s) can occur immediately, gradually or at a specified time, as described above. As a result, they make contact with and bind HIV and reduce or prevent viral entry into cells.

Fusion proteins of the present invention comprise a soluble, trimeric form or version of a coiled-coil, such as a soluble, trimeric form or version of a coiled-coil region of a protein (of non-HIV origin or of HIV origin) and a sufficient portion of the C-terminal end of the N-peptide of HIV gp41 to bind to the C-peptide region. In one embodiment, the portion of the C-terminal end of the N-peptide comprises sufficient amino acid residues to bind to the C-peptide region and include the HIV coiled-coil cavity or hydrophobic pocket (the pocket-comprising residues of the N-peptide). The N-peptide of HIV gp41 can be that of HIV-1, HIV-2, another HIV strain or a strain from another species (e.g., simian immunodeficiency virus (SIV), feline immunodeficiency virus or Visna virus). For example, HIV-2 sequence LLRLTVWGTKNLQARVT (SEQ ID NO: 26), SIV sequence LLRLTVWGTKNLQTRVT (SEQ ID NO: 27) or a sequence comprising invariant residues in HIV-1, HIV-2 and SIV (represented LLXLTVWGXKXLQXRXX (SEQ ID NO: 28), wherein amino acid residues L, T, V, W, G, K, Q, and R are the single letter code used for amino acid residues and X can be any amino acid residue). Also the subject of this invention is a soluble trimeric model of the HIV gp41 hydrophobic pocket, which can be a D-peptide or an L-peptide and comprises a soluble trimeric coiled-coil and a sufficient portion of the N-peptide region of HIV gp41 to comprise the amino acid residues which form the pocket of the N-helix coiled-coil region of HIV gp41. The D- or L-peptide can comprise, as the soluble, trimeric coiled-coil, the coiled-coil of GCN4-pI$_Q$I; GCN4-pII; Moloney Murine Leukemia Virus or the ABC heterotrimer. The component which is a sufficient portion of the N-peptide of HIV gp41 to comprise the amino acid residues of the pocket can comprise, for example: LLQLTVWGIKQLQARIL of HIV-1 (SEQ ID NO: 18); LLRLTVWGTKNLQARVT of HIV-2 (SEQ ID NO: 26); LRLTVWGTKNTLQTRVT of SIV (SEQ ID NO: 27) or the invariant residues of these, which are:

LLXLTVWGXKXLQXRXX.    (SEQ ID NO: 28)

One embodiment of the instant invention is fusion proteins in which the components are a trimeric version of the coiled-coil region of a protein (such as GCN4-pI$_Q$I) and the N-helix coiled-coil of HIV gp41 that include all, part or none of the N-helix cavity. That is, a fusion protein of the present invention can comprise a trimeric form of the coiled-coil region of GCN4-pI$_Q$I and a portion of the N-peptide of HIV-1 gp41, wherein the portion of the N-peptide of gp41 comprises part, or all, or none of the N-helix cavity of HIV-I gp41. For example, a fusion protein can be made that contains residues from GCNL4-pI$_Q$I and residues from N36. The fusion protein, denoted IQN24n, contains 29 residues of GCN4-pI$_Q$I, including three mutations for increased solubility, and 24 residues from the N-terminal end of N36 (SGIVQQQNNLLRAIEAQQHLLQLT) (SEQ ID NO: 29); for recombinant expression in E. coli, an extra Met residue is included at the N-terminus. For example, a fusion protein can comprise a portion of the N-peptide of HIV gp41 comprising the amino acid sequence of (SEQ ID NO: 29). The sequence of IQN24n is: MRMKQIEDKIEEIESKQKKIENEIARIKKLISGIVQQQNNLLRAIEAQQHLLQLT (SEQ ID NO: 30). This fusion protein can be made by a variety of methods, including chemical synthesis or recombinant DNA methods or by recombinant expression in E. coli, in which case the N- and C-termini are not blocked. Because the superhelix parameters of the GCN4-pIQI coiled-coil are nearly identical to the HIV gp41 N-helix coiled-coil, the resulting fusion protein molecule IQN24n is predicted to form a long trimeric coiled-coil, which presents part of the gp41 N-helix coiled-coil as a trimer (not aggregated).

The same strategy described herein to solve this problem for the gp41 hydrophobic pocket can be applied towards the development of soluble, trimenic models of the gp41 N-helix coiled-coil region. in general. Such trimeric models (including IQN17, but also including, for example, peptides that do not contain the pocket residues of gp41) can be used as inhibitors.

Any of a wide variety of variations can be made in the GCN4-pIQI component of fusion proteins described herein (e.g., IQN17 or IQN24n) and used in the method, provided that these changes do not alter the trimeric state of the coiled-coil. Changes can also be made in the amino acid composition of the fusion protein component which is the portion from the HIV gp41 N36 peptide, to produce variants (e.g., variants of IQN17 or IQN24n). There is no limit to the number or types of amino acid residue changes possible, provided that the trimeric state of the coiled-coil and the structure of the surface of the fusion protein corresponding to the N-peptide coiled coil of HIVgp41 are maintained. The fusion protein component which is the portion of the HIV gp41-peptide can include all, part, or none of the N-helix cavity. For example, other parts of N51, N36, DP-107, or other regions of the HIV gp41 N-helix region can be fused to GCN4-pI$_O$I (or another trimeric version of the coiled-coil region of a protein) to generate trimeric (not aggregated) helical coiled-coil fusion proteins and used in the method. There is no limit to the number or types of fusion proteins that can be designed and generated, provided that the trimeric state of the coiled-coil and the structure of the surface of the fusion protein corresponding to the N-peptide coiled coil of HIV gp41 are maintained. Such fusion proteins can be designed and generated using methods known to those of skill in the art, such as evaluating heptad-repeat positions or superhelix parameters of coiled coils.

IQN17 is useful as an anti-HIV therapeutic agent, a prophylactic agent or drug to prevent HIV infection, a reagent for identification (screening for) or designing other anti-HIV therapeutics or prophylactics, and an immunogen to elicit antibodies that prevent HIV infection.

Applicants have shown that a portion of the N-peptide can be solublized by addition of a soluble, trimeric coiled-coil, GCN4-pI$_O$I. The resulting molecule is stable under physiological conditions and is correctly folded such that IQN17 presents a surface that is structurally complementary to the C-peptide region of HIV gp41. Further, IQN17 and similar molecules can be assessed for their ability to bind to the C-helical region of gp41, and inhibit its function. The N-helical core of gp41 is highly conserved (in terms of amino acid composition) and thus, it is likely that IQN17 and variants thereof will be broadly neutralizing against a variety of clinical HIV strains and, thus, useful therapeutically.

IQN17, which is based upon the known structure of the gp41 ectodomain, consists, in one embodiment, of three N-peptides joined to (or present in larger molecule with) a soluble trimeric coiled-coil and arranged to fold into a substantial part of the N-helical core with peptide biding sites of the N-peptides exposed.

IQN17 protein can be produced by a variety of methods. For example, it can be chemically synthesized. Alternatively, it can be produced, using known methods and expression systems, by expressing IQN17 protein-encoding DNA, which can be a single DNA that encodes the entire IQN17 protein. Alternatively, protein synthetic methods can be used to produce IQN17 protein.

IQ(IN) peptides can have a wide variety of sequences, both in the N-helix and fused coiled-coil components, and can be comprised of L-amino acid residues, D-amino acid residues and modified amino acids residues. IQN17 can include amino acid residues in addition to those of the helices and the fused coiled-core (e.g., to stabilize the molecule). It is likely that the IQN17 described here can be altered to enhance stability and activity. Minor changes in the fused coiled-coil and the exact borders of the N-Helix are likely to have significant effects on the stability, yield, and activity of IQN17.

As currently constructed, IQN17 exposes a portions of three C-peptide binding sites. A strategy for exposing longer segments of the C-peptide binding site on IQN17 (or related molecules) involves extending the N-peptide region of IQN17.

IQN17 is useful in a variety of contexts. As described herein, IQN17 is a potent inhibitor of viral membrane fusion, and, thus, acts on the virus before it enters the cell (unlike current practical therapy, which acts on HIV-infected cells). IQN17 is quite soluble and has been shown to be stable under the conditions described herein. It is reasonable to expect that its size will prevent rapid filtration in the kidney. In addition, IQN17 dimers can be made by disulfide crosslinking, to produce a molecule filtered to a lesser extent than the IQN17 "monomer". Thus, it is reasonable to expect that dimers have an enhanced bioavailability when compared to the C-peptides.

IQN17 prevents virus from entering cells, unlike standard therapy that targets viral proteins after viral entry, and thus, IQN17 can be used prophylactically to prevent infection or reduce the extent to which infection occurs. One use for such a therapeutic is in the event of a needlestick injury, such as might occur in a hospital or in settings in which needles contaminated with HIV are shared.

In one embodiment of the present invention, IQN17 is used to reduce HIV infection in an individual. In this embodiment, IQN17 is administered, either as IQN17 itself or via expression of IQN17-encoding DNA in appropriate host cells or vectors, to an individual in sufficient quantity to reduce (totally or partially) HIV infection of the individual's cells. That is, a dose of IQN17 sufficient to reduce HIV infection (an effective dose) is administered in such a manner (e.g., by injection, topical administration, intravenous route that it inhibits (totally or partially) HIV entry into cells. In one embodiment, a gene therapy approach is used to provide the effective dose, by introducing cells that express IQN17 protein into an individual. IQN17 can be administered to an individual who is HIV infected, to reduce further infection, or to an uninfected individual, to reduce infection.

The serum stability of IQN17 can be tested, using known methods to ascertain its therapeutic potential.

The outside surface of the fusion coiled-coil of IQN17 can be varied, for example, to enhance bioavailability, decrease toxicity, and avoid immune clearance. IQN17 exhibits potent inhibitory activity and GCN4-pI$_O$I does not, it is the exposed N-peptide region that is responsible for inhibition. The rest of the molecule provides a scaffold for displaying the N-peptide. Therefore, this scaffold can be modified without adversely affecting the inhibitory activity of IQN17. Modification of the scaffold may provide several advantages. First, it would facilitate procedures in which multiple administrations of IQN17 are required. For example, when IQN17 is used as an anti-HIV therapeutic agent, multiple doses might be required. After extended administration, individuals might develop antibodies to IQN17 which are likely to increase its clearance from the body. The availability of multiple versions of IQN17 would help to circumvent this problem by evading preexisting antibodies. Second, it may be possible to design versions of IQN17, for example by introducing glycosylation sites on the external surface, in which the scaffold is less immunogenic.

The trimer of helical hairpins (TOH) is a common feature of many viral membrane fusion proteins (Singh, M. et al. J. Mol. Biol. 290, 1031-1041 (1999)). It has been observed in crystal structures of influenza, Ebola SV5 (simian parainfluenza virus 5), and RSV (human respiratory syncitial virus). In addition, many other members of the retrovirus, paramyxovirus, and filovirus families are predicted to contain this motif. A similar structure has been observed in the associated vertebrate vesicle fusion proteins and may be found in spermegg, fertilization proteins. The basic strategy described herein can be applied to any of these systems in order to inhibit fusion.

The present invention is illustrated by the following examples, which are not intended to be limiting in any way.

EXAMPLE 1

Assessment of the Specificity of IQN/Peptide Interaction and of Inhibition by IQN Peptide of Membrane Fusion Assays were carried out to assess the ability of IQN17 to interact with the C-region of gp41 and inhibit function of the fusion protein. This inhibition of membrane fusion by IQN17 and IQN23 and GCN4-$pI_QI$ was assessed using a cell based assay. Proteins IQN17, IQN23 and GCN4-$pI_QI$ are serially diluted in modified DMEM media with 5% FCS and aliquoted into slide chambers. HELA cells ($4 \times 10^4$) expressing CD4 and coreceptor and containing a βgalactosidase gene under the control of the Tat promoter are added. CHO cells ($2 \times 10^4$) expressing gp160 (precursor protein to gp120/gp41) and Tat are also added. The 400 µl miniculture is incubated at 37° for 8 to 24 hours; fused cells (syncytia) will transcribe and translate β-galactosidase. The cells are fixed in gluteraldehyde and exposed to X-gal/Fe solution for one hour. Syncytia that contain P-galactosidase turn blue-green. In this assay, IQN17 demonstrates a potent inhibition of syncytia formation, with an $IC_{50}$ of 20-80 nM.

The inhibitory potentials of IQN17, IQN23 and GCN4-$pI_QI$ have been reproduced in viral fusion experiments. HIV, modified to contain a luciferase reporter gene, is mixed with HOS cells expressing CD4 and coreceptor in the presence of diluted protein for 6 hours at 37° C. (Chan et al., Cell, 93, 681-684 (1998)). The virus solution is replaced, and the HOS culture is incubated 48 hours more in fresh media. Luciferase activity is measured in a luminometer. In this assay, IQN17 inhibits luciferase activity with an $IC_{50}$ of approximately 250 nM; IQN23 with an $IC_{50}$ of approximately 80 nM. Again, GCN4-$pI_QI$ shows no appreciable block up to ~10 µM.

EXAMPLE 2

Assessment of Inhibition of Infectivity

Materials and Methods

Peptide Synthesis and Purification. All peptides were chemically synthesized on a PE Biosystems 431A peptide synthesizer upgraded with feedback monitoring. The standard Fmoc/HBTU chemistry (Fields et al., 1991) was modified with DMSO/NMP resin swelling and acetic anhydride capping after every couple. The peptides were cleaved from the PE Biosystems Pal resin with Reagent K. Each peptide has an acetylated N terminus and a C-terminal amide.

The sequence of IQN17 is as described previously (Eckert et al.): Ac-RMKQIEDKIEEIESKQKKIENEIARIKK LLQLTVWGIKOLQARIL-$NH_2$ (SEQ ID NO:1). The first 29 residues are a non-natural designed trimeric coiled-coil, and the final seventeen residues are derived from the N-peptide region of HXB2 gp41 (underlined). Sequential heptads were removed from the N-terminus of IQN17 to yield three increasingly shorter peptides: $IQ_{22}N17$ (Ac-KIEEIESQK-KIENEIARIKKLLQLTVWGIKQLQARIL-$NH_2$) (SEQ ID NO: 8), $IQ_{15}N17$ (Ac-KQKKIENEIARIKK LLQLTVWGIKQLQARIL-$NH_2$) (SEQ ID NO: 6) and $IQ_8N17$ (Ac-EIARIKKLLQLTVWGIKQLQARIL-$NH_2$) (SEQ ID NO: 5). More stable versions of the $IQ_{22}N17$ and $IQ_{15}N17$ peptides were made by changing the glutamine residues to isoleucines. These peptides are called $II_{22}N17$ and $II_{15}N17$, respectively. Also, longer IQN17 derivatives were made by inserting additional residues from the HXB2 gp41 N-peptide region, taking care to keep the coiled-coil register in tact. These peptides are IQN23 (Ac-RMKQIEDKIEE-IESKQKKIENEIARIKKL IEAQQHLLOLTVWGIKQLQARIL-$NH_2$) (SEQ ID NO: 2), IQN36 (Ac-RMKQIEDKIEEIESKQKKIENEIARIKKLI SGIVQQQNNLLRAIEAQQHLLQLTVWGIKQLQARIL-$NH_2$) (SEQ ID NO: 4), and IQN26 (Ac-RMKQIEDKIEE-IESKQYKIENEIARIKKLIVQARQLLSGIVQQQNNL-LRAIEAQQH-$NH_2$ (SEQ ID NO: 13). Finally, an additional derivative of IQN17 was made in which an entirely different designed trimeric coiled-coil was placed N-terminal to the gp41-derived residues. The coiled-coil was based on a design described by Tanaka et al., but has significant alterations in the e and g positions and an I to Q substitution at an a position. The sequence of this peptide, called IZN17, is Ac-IKKEIEAIKKEQEAIKKKIE AIEK LLOLTVWGIKQLQARIL-$NH_2$ (SEQ ID NO: 31). Additional peptides that are being studied for their inhibitory activity are: IZN23 (Ac-IKKEIEAIKKEQEAIKK-KIEAIEKEIEAQQHLLQLTVWGIKQLQARIL-$NH_2$) (SEQ ID NO: 32), IZN36 (Ac-IKKEIEAIKKEQEAIKK-KIEAIEKEISGIVQQQNNLL-RAIEAQQHLLQLTVWGIKQLQARIL-$NH_2$) (SEQ ID NO: 33) and IZN26: (Ac-YGGIKKEIEAIKKEQEAIKK-KIEAIEKEIVQARQLLSGIVQQQNNLLRAIEAQQH-$NH_2$ (SEQ ID NO: 14).

Following cleavage from the resin, each peptide was desalted over a Sephadex G-25 column (Pharmacia) and lyophilized. It was then resuspended in 5% acetic acid and purified over a Vydac C18 preparative column on a reverse phase high-performance liquid chromatography apparatus (Waters, Inc.). The peptide was eluted from the column with a water-acetonitrile gradient in the presence of 0.1% trifluoroacetic acid and then lyophilized. The molecular weights of each peptide were validated using MALDI-TOF mass spectrometry (PerSeptive Biosystems).

Circular Dichroism. All CD measurements were performed on an Aviv 62 DS circular dichroism spectrometer. Standard scans were performed on 10 µM solutions of peptide in PBS (50 mM sodium phosphate, 150 mM sodium chloride [pH 7.4]) from 200 to 260 nm in a 1 cm pathlength cuvette with a 5 second averaging time. The mean residue ellipticity θ was calculated by dividing the raw signal by peptide concentration (M), pathlength (mm) and number of amino acids. Percent helicity was calculated according to Chen et al. (Biochemistry, 13, 1974, p 3350). Thermal denaturation scans of 10 µM peptide solutions in PBS were recorded at 222 nm. The peptide was heated at two degree intervals starting at 4° C., with an equilibration time of 1.5 minutes and an averaging time of 60 seconds.

Sedimentation Equilibrium. All measurements were recorded on a Beckman XL-A analytical ultracentrifuge equipped with an An-60 Ti rotor. Lyophilized peptide was resuspended in water, and the peptide concentration was determined (Edelhoch, 1967). The solution was diluted to 100-200 µM and then dialized overnight against PBS. Following dialysis, the concentration was redetermined and the appropriate dilutions were made, using the dialysis buffer. The samples were centrifuged at speeds ranging from 19,000 to 25,000 RPM.

HIV Infectivity Assay. Inhibitory activity of IQN17 and derivatives was determined in an HIV luciferase assay (Chen et al., 1994). Specifically, virus was made by cotransfecting 293T cells with an HIV-1 genome containing a frame-shift mutation in env and luciferase replacing the nef gene (NL43LucR-E-) along with pCMVHXB2, an expression vector with the HXB2 gp160 gene. The resultant virus is only viable for one round of infection since its genome lacks the envelope gene. The cellular debris was removed by low-speed centrifugation. The remaining viral supernatant was used to infect HOS-CD4/Fusion cells (N. Landau, National Institutes of Health AIDS Reagent Program) in the presence of the potentially inhibitory peptides. Two days post-infection, the cells were lysed and luciferase activity was monitored on a Wallac AutoLumat LB953 luminometer (Gaithersburg, Md.). $IC_{50}$s (the peptide concentration at which half of the viral infection is inhibited) were calculated by fitting the data to a Langmuir equation $[y=k/(1+[peptide]/IC_{50})]$, where y=luciferase activity and k is a scaling constant.

Results

The pocket-forming region of the N peptide inhibit as a coiled-coil trimer. The x-ray crystal structure of fusogenic gp41 shows a coiled-coil trimer of N peptides surrounded by three helical C peptides. A hydrophobic pocket at the base of the N peptides, into which three hydrophobic side chains from the each of the C peptides pack, has been shown to be an important target for anti-HIV-1 compounds. IQN17 is a chimeric molecule designed to accurately present this hydrophobic pocket in its proper trimeric coiled coil conformation, in the absence of C peptides (Eckert et al.). A designed trimeric coiled coil, GCN4-$pI_QI'$, was fused to the N-terminus of seventeen residues of the N-peptide. These seventeen residues span the pocket region of the N peptide. Coiled coils are composed of a characteristic repeat of seven residues (designated a through g), with the first (a) and fourth (d) positions typically occupied by hydrophobic side chains. Careful attention was taken to fuse the GCN4 portion and the N-peptide portion in proper coiled coil register. Here, we assayed the inhibitory activity of this chimeric molecule, and determined that this activity is reliant on the coiled coil conformation.

Two synthetic peptides were compared: N17, containing the seventeen residues of the N peptide that comprise the hydrophobic pocket, and IQN17. N17 is difficult to get into solution—it precipitates. Therefore it is unlikely to be a discretely trimeric coiled coil. Alternatively, IQN17 is easily dissolved. It is a fully helical and discretely trimeric species at 20 μM. IQN17 is extremely stable, with a melting temperature above 100° C. Both peptides were assayed for their ability to inhibit viral infection. N17 does inhibit infection, but has an $IC_{50}$ of approximately 10 μM. IQN17 inhibits infectivity at approximately two orders of magnitude lower concentrations, with an $IC_{50}$ of approximately 180 nM. Therefore, the inhibitory activity of the N17 region of the N peptide is greatly enhanced in a trimeric coiled-coil conformation.

The pocket of IQN17 contains the inhibitory activity. To rule out the possibility that the IQ-portion of IQN17 is responsible for all or some of the inhibitory activity, two control molecules were studied. These peptides are GCN4-$pI_QI'$ and IQN17 (G572D). GCN4-$pI_QI'$ consists of only the IQ portion of IQN17. IQN17 (G572D) contains a mutation in the lining of the hydrophobic pocket. A glycine residue is changed to aspartate, introducing a charge into the otherwise hydrophobic environment. Both of these molecules are helical as determined by circular dichroism, and therefore serve as proper controls, structurally. In infectivity assays, they have little, if any inhibitory activity. GCN4-$pI_QI'$ does not inhibit at any concentrations tested (so far up to 10 μM), and the $IC_{50}$ of the IQN17 (G572D) is about 20 μM. Therefore the hydrophobic pocket of IQN17 is responsible for the inhibitory activity of IQN17, with the IQ portion likely serving to present the pocket in the proper conformation.

The inhibitory potency of IQN17 is correlated to its stability. A series of peptides were studied to determine how much of the IQ portion of the molecule is required for the coiled coil structure and inhibitory activity of IQN17. Groups of seven residues were sequentially removed from the N-terminus of IQN17 to make peptides of 38, 31 and 24 amino acids in length ($IQ_{22}N17$, $IQ_{15}N17$ and $IQ_8N17$, respectively). $IQ_{22}N17$ showed a characteristic alpha helical CD spectrum at 10 μM with a minimum of approximately $-36,000$ deg cm$^2$ dmol$^{-1}$ at 222 nm. Not suprisingly, it is much less stable than wild type IQN17, with a melting temperature below 80° C. at 10 μM (IQN17 has a melting temperature above 100° C. at the same concentration). $IQ_{15}N17$, which is seven residues shorter than $IQ_{22}N17$, is slightly less helical with a minimum of approximately $-27,000$ deg cm$^2$ dmol$^{-1}$ at 222 nm. Also, the minimum at 208 nm is slightly lower than that at 222 nm, implying a partial unfolding of this peptide. Its thermal stability is about 10 degrees lower than that of $IQ_{22}N17$. Finally, circular dichroism studies of $IQ_8N17$ show a much lower minimum at 208 than at 222 nm, implying that this peptide is not very helical. It is also much less stable than the first two peptides. The inhibitory activity of each of these peptides is significantly lower than that of wild type IQN17, despite the fact that $IQ_{22}N17$ is as helical as IQN17 at 10 μM. The $IC_{50}$ of $IQ_{22}N17$ for viral infectivity is around 1 μM, and the $IC_{50}$s of the two shorter molecules is close to 10 μM (very similar to the inhibitory activity of N17). Since $IQ_{22}N17$ is much less stable than IQN17, it is likely that it is unfolded at the lower concentrations in which IQN17 demonstrates inhibitory potency.

To determine if it is lowered stability that has negatively affected the inhibitory activity of $IQ_{22}N17$ and $IQ_{15}N17$, two additional peptides were made in which the glutamine in the a position of the IQ portion of the above two molecules was mutated to isoleucine. Previously it had been shown that mutating an isoleucine to a glutamine in the core of a trimeric coiled coil drastically reduces the stability of the coiled coil (Eckert, Malashkevich, Kim). These additional peptides are called $II_{22}N17$ and $II_{15}N17$. $II_{22}N17$ is extremely helical at 10 μM, with an approximate 222 nm minimum of $-41,000$ deg cm$^2$ dmol$^{-1}$. $II_{15}N17$ is slightly less helical with an approximate $-33,000$ deg cm$^2$ dmol$^{-1}$ minimum. As with $IQ_{15}N17$, the 208 nm minimum is slightly lower than the 222 nm minimum. The stability of these peptides and their inhibitory activity is increased relative to the glutamine versions. At 10 μM, $II_{22}N17$ is not melted even at 100° C. and its $IC_{50}$ is approximately 170 nM. $II_{15}N17$ is more stable than $IQ_{15}N17$, and its $IC_{50}$ is approximately 3 μM. Therefore it seems likely that the inhibitory activity of the peptides is correlated to the stability of the coiled-coil structures.

Increasing the length of the N peptide region does not necessarily increase inhibitory potency. Since IQN17 has a binding site for the C peptide region of gp41, it likely inhibits by binding to this region during the process of viral membrane fusion. Therefore, it is possible that by extending the length of the N-peptide region, thereby increasing the C peptide binding area, the inhibitory activity will improve. To test this hypothesis two additional peptides, IQN23 and IQN36, were constructed. They have seven and 19 additional residues from gp41, N-terminal to the pocket region, respectively. Analytical ultracentrifugation studies show that these peptides are more aggregated than IQN17 (with Mobs/Mcalc of 3.3 for IQN23 and 3.5 for IQN36 at 20 μM). The $IC_{50}$ of IQN23 is about 30 nM, and IQN36 has an $IC_{50}$ of approximately 50 nM. N36, just the gp41 region of IQN36, has an $IC_{50}$ of around 1 μM, as comparison. By increasing the gp41 residues from 17 to 23, there was an approximate 6-fold gain in inhibitory activity. Likewise, by increasing the residues from 17 to 36, there is a 3-fold gain. However, IQN23 is more potent than IQN36. Therefore, the inhibitory activity does not increase just due to adding N peptide residues. There is likely a trade-off between C-peptide binding energy and aggregation state. The longer the N peptide region is, the more aggregated the molecule is, and it therefore more poorly represents a discretely trimeric C peptide binding site.

The pocket region of the N peptide is not required for inhibitory activity. To determine if the pocket region was required for the inhibitory potency of the chimeric N peptide molecules, an additional peptide was made, IQN26. This peptide contains 26 residues of the N peptide region N-terminal to the hydrophobic pocket. Circular dichroism studies show it is helical, and sedimentation equilibrium studies show it is slightly aggregated. It does have potent inhibitory activity. Therefore, the N peptide region, when constrained in a coiled coil formation, has inhibitory activity even in the absence of the hydrophobic pocket region.

An alternate, more stable peptide, IZN17, is a more potent inhibitor. We studied an additional IQN17 derivative, in which the IQ portion of the molecule was replaced with another trimeric designed coiled coil. This coiled coil, called 'IZ' for isoleucine zipper, is based on a design described by Tanaka, et al., but has several changes in the e and g positions and an isoleucine to glutamine substitutation at an a position. The resulting peptide is termed IZN17. IZN17 is helical and discretely trimeric at 20 μM as determined by circular dichroism and sedimentation equilibrium, respectively. Interestingly, IZN17 has an $IC_{50}$ of approximately 5.6 nM in the viral infectivity assay, and is therefore a much better inhibitor than IQN17. There are two potential reasons for this increase in potency. First, IZN17 is likely more stable than IQN17, and therefore stays folded at lower concentration. Both peptides melt above 100° C., although thermal unfolding transitions can be seen in the presence of denaturant. In 2 M GuHCl, the thermal denaturation temperature of IZN17 is ten degrees higher than that of IQN17. Second, IZN17 contains two additional residues from the gp41 N peptide region, due to a coincidence in sequence between IZ and gp41. This could provide an increase in binding energy to the C peptide region of gp41.

The inhibitory activity of IZN23, IZN36 and IZN26 can be tested using known methods, such as those described herein. These peptides are likely to be potent inhibitors of HIV-1 infection.

The following Table summarizes the biophysical data and inhibitory activity for the chimeric coiled coil N peptides. The first column ($\theta_{222nm}$) is circular dichroism data, representing the helicity of each peptide. The lower the number, the more helical. The second column is the melting temperature and signifies the temperature at which half of the peptide is unfolded. The next column ($M_{obs}/M_{calc}$) signifies the oligomeric state of the peptide, with 3.0 being a discrete trimer. The final column is the concentration at which each peptide is at half maximal inhibitory potency for viral infection. Table 1. Biophysical data and HIV-1 inhibitory activity of IQN17 and derivatives.

TABLE 1

Biophysical data and HIV-1 inhibitory activity of IQN17 and derivatives.

| PEPTIDE | $\Theta_{222\ nm}$ (deg cm$^2$ dmol$^{-1}$) | Melting Temperature (° C.) | $M_{obs}/M_{calc}$ | $IC_{50}$ (nm) |
|---|---|---|---|---|
| IQN17 | ~−36,000 | >100 | 3.15 | ~180 |
| N17 | n.d. | n.d. | n.d. | ~10,000 |
| GCN4-p$I_Q$I' | ~−31,000 | 68 | 3.00 | >10,000 |
| IQN17(G572D) | ~−39,000 | n.d. | n.d. | ~20,000 |
| $IQ_{22}N17$ | ~−36,000 | ~76 | 2.73* | ~1,000 |
| $IQ_{15}N17$ | ~−27,000 | ~64 | n.d. | ~10,000 |
| $IQ_8N17$ | n.d. | n.d. | n.d. | ~10,000 |
| $II_{22}N17$ | ~−41,000 | >100 | 3.02 | ~170 |
| $II_{15}N17$ | ~−33,000 | ~76 | 2.64 | ~3,000 |
| IQN23 | n.d. | n.d. | 3.29 | ~30 |
| N23 | n.d. | n.d. | n.d. | n.d. |
| IQN36 | n.d. | n.d. | 3.47 | ~50 |
| N36 | n.d. | n.d. | n.d. | ~1,000 |
| IQN26 | ~25,000 | ~70 | 3.25 | ~43 |
| IZN17 | ~−31,000 | >100 | 3.05 | 5.6 |
| IZN23 | n.d. | n.d. | n.d. | n.d. |
| IZN36 | n.d. | n.d. | n.d. | n.d. |
| IZN26 | ~33,000 | ~82 | ~2.87 | n.d. |

*this was determined at 50 μM

Legend:

Table 1 lists all of the peptides studied in this paper. The first column gives the name of the peptide. The second column is the ellipticity at 222 nm of a 20 μM solution of peptide in PBS. The third column lists the midpoint of thermal denaturation of 10 μM solutions of peptide in PBS. The fourth column gives the ratio of the observed molecular weight of 20 μM peptide solutions in PBS by analytical ultracentrifugation to the calculated molecular weight for a monomeric peptide. The final column give the concentration of peptide at which half of viral infectivity is inhibited ($IC_{50}$).

While this invention has been particularly shown and described with references to preferred embodiments thereof, it will be understood by those skilled in the art that various changes in form and details may be made therein without departing from the scope of the invention encompassed by the appended claims.

What is claimed is:

1. A soluble trimeric coiled-coil peptide comprising an isoleucine zipper (IZ) trimeric coiled-coil peptide and a portion of the HIV gp41 N-helix coiled-coil, wherein the portion of the HIV gp41 N-helix coiled-coil binds to the C-peptide region of HIV gp41.

2. The soluble trimeric coiled-coil peptide of claim 1, wherein the isoleucine zipper (IZ) trimeric coiled-coil peptide comprises an amino acid sequence selected from the group consisting of: YGGIKKEIEAIKKEQEAIKK-KIEAIEKEIEA (SEQ ID NO: 11); YGGIEKKIEAIEK-KIEAIEKKIEAIEKKIEA (SEQ ID NO: 16); or amino acids 1-24 of SEQ ID NO: 31.

3. The soluble trimeric coiled-coil peptide of claim 1, wherein the portion of the HIV gp41 N-helix coiled-coil comprises the amino acid sequence: LLXLTVWGXKX-LQXRXX (SEQ ID NO: 28), wherein amino acid residues L, T, V, W, G, K, Q, and R are the single letter code used for amino acid residues and X can be any amino acid residue.

4. The soluble trimeric coiled-coil peptide of claim 3, wherein the amino acid sequence of the portion of the HIV gp41 N-helix coiled-coil is selected from the group consisting of: SEQ ID NO: 18, SEQ ID NO: 26, SEQ ID NO: 27, SEQ ID NO: 34, and SEQ ID NO: 35.

5. The soluble trimeric coiled-coil peptide of claim 1, wherein the amino acid sequence of the soluble trimeric coiled-coil peptide is selected from the group consisting of IZN17 (SEQ ID NO: 31), IZN23 (SEQ ID NO: 32), or IZN36 (SEQ ID NO: 33).

6. A soluble trimeric coiled-coil comprising a peptide IQN36, wherein the amino acid sequence of IQN36 is:
RMKQIEDKIEEIESKQKKIENEIARIKK-
LISGIVQQQNNLLRAIEAQQHLLQLTVWG
IKQLQARIL (SEQ ID NO: 4).

7. A soluble trimeric coiled-coil consisting of a peptide IQN36, wherein the amino acid sequence of IQN36 is:
RMKQIEDKIEEIESKQKKIENEIARIKK-
LISGIVQQQNNLLRAIEAQQHLLQLTVWG
IKQLQARIL (SEQ ID NO: 4).

8. A soluble trimeric coiled-coil comprising a peptide IZN36, wherein the amino acid sequence of IZN36 is:

IKKEIEAIKKEQEAIKKKIEAIEKEIS-GIVQQQNNLLRAIEAQQHLLQLTVWGIKQLQARIL (SEQ ID NO: 33).

9. A soluble trimeric coiled-coil consisting of a peptide IZN36, wherein the amino acid sequence of IZN36 is: IKKEIEAIKKEQEAIKKKIEAIEKEIS-GIVQQQNNLLRAIEAQQHLLQLTVWGIKQLQARIL (SEQ ID NO: 33).

* * * * *